(12) United States Patent
Cevc

(10) Patent No.: US 7,175,850 B2
(45) Date of Patent: Feb. 13, 2007

(54) FORMULATION FOR TOPICAL NON-INVASIVE APPLICATION IN VIVO

(75) Inventor: Gregor Cevc, Kirchheim (DE)

(73) Assignee: Idea AG, Munich (DE)

( * ) Notice: Subject to any disclaimer, the term of this patent is extended or adjusted under 35 U.S.C. 154(b) by 0 days.

(21) Appl. No.: 09/887,493

(22) Filed: Jun. 22, 2001

(65) Prior Publication Data

US 2002/0064524 A1 May 30, 2002

Related U.S. Application Data

(63) Continuation of application No. PCT/EP98/08421, filed on Dec. 23, 1998.

(51) Int. Cl.
*A61K 8/02* (2006.01)

(52) U.S. Cl. .................... 424/401; 424/450

(58) Field of Classification Search ......... 424/401–450
See application file for complete search history.

(56) References Cited

U.S. PATENT DOCUMENTS

| | | | |
|---|---|---|---|
| 4,333,927 A | 6/1982 | Ofuchi et al. | |
| 4,427,670 A | 1/1984 | Ofuchi et al. | |
| 4,619,794 A | 10/1986 | Hauser | |
| 4,814,161 A | 3/1989 | Jinks et al. | |
| 4,911,928 A | 3/1990 | Wallach | |
| 4,921,706 A | 5/1990 | Roberts et al. | |
| 4,937,078 A | 6/1990 | Mezei et al. | |
| RE33,273 E | 7/1990 | Speaker | |
| 4,944,948 A | 7/1990 | Uster et al. | |
| 4,954,345 A | 9/1990 | Müller | |
| 5,238,613 A | 8/1993 | Anderson | |
| 5,322,685 A * | 6/1994 | Nakagawa et al. | |
| 5,607,692 A | 3/1997 | Ribier et al. | |
| 5,741,515 A | 4/1998 | Ciceri et al. | |
| 5,958,379 A | 9/1999 | Regenold et al. | |
| 6,562,370 B2 | 5/2003 | Luo et al. | |
| 6,582,724 B2 | 6/2003 | Hsu et al. | |
| 6,586,000 B2 | 7/2003 | Luo et al. | |
| 6,645,520 B2 | 11/2003 | Hsu et al. | |
| 6,835,392 B2 | 12/2004 | Hsu et al. | |
| 2002/0048596 A1 | 4/2002 | Cevc | |

FOREIGN PATENT DOCUMENTS

| | | |
|---|---|---|
| AU | 1740283 | 7/1983 |
| AU | 724218 | 10/1996 |
| CA | 1 143 656 | 3/1983 |
| CA | 1289420 | 9/1991 |
| CA | 2052164 | 9/1992 |
| DE | 3016976 | 11/1980 |
| DE | 3713494 | 10/1987 |
| DE | 40 26 833.0 | 8/1990 |
| DE | 44 47 287 | 11/1996 |
| DE | 4447287 | 11/1996 |
| EP | 0 088 046 | 2/1983 |
| EP | 0 102 324 | 7/1983 |
| EP | 0102324 | 3/1984 |
| EP | 0 152 379 | 2/1985 |
| EP | 0224837 | 11/1986 |
| EP | 0211647 | 2/1987 |
| EP | 0220797 | 5/1987 |
| EP | 0 298 280 | 6/1988 |
| EP | 0280492 | 8/1988 |
| EP | 0 393 707 | 4/1990 |
| EP | 0 475 160 | 8/1991 |
| EP | 0475160 | 3/1992 |
| EP | 0 355 095 | 8/1993 |
| EP | 0674913 | 10/1995 |
| EP | 0704206 | 4/1996 |
| EP | 0707847 | 4/1996 |
| EP | 0 382 716 | 1/1998 |
| EP | 0 995 435 | 4/2000 |
| HU | 9903363 | 3/2000 |
| HU | 0104424 | 3/2002 |
| HU | 0105400 | 5/2002 |
| JP | 61-271204 | 12/1986 |
| JP | 07-324029 | 12/1995 |
| WO | WO-81/02673 | 10/1981 |
| WO | WO 87/01938 | 4/1987 |

(Continued)

OTHER PUBLICATIONS

English translation of German Pat. No. 44 47 287 C1 (1996).*
Journal of Controlled Release (Apr. 1997) vol. 45, No. 3, table of contents.*
G. Cevc et al., Transdermal drug carriers: basic properties, optimization and transfer efficiency in the case of epicutaneously applied peptides, *J. Contr. Rel.*, 36, pp. 3-16, 1995.
S. Yuan, et al., Cationic Liposome and Gene Transfer, *Progress in Physiological Science*, 28(2), pp. 163-165, 1997.

(Continued)

*Primary Examiner*—Susan Coe Hoffman
(74) *Attorney, Agent, or Firm*—Edwards Angell Palmer & Dodge LLP; Peter F. Corless; Lisa Swiszcz Hazzard

(57) ABSTRACT

A formulation comprising molecular arrangements capable of penetrating pores in a barrier, owing to penetrant adaptability, despite the fact that the average diameter of said pores is smaller than the average penetrant diameter, provided that the penetrants can transport agents or else enable agent permeation through the pores after penetrants have entered pores, characterized in that the formulation comprises at least one consistency builder in an amount that increases the formulation to maximally 5 Nm/s so that spreading over, and retention at, the application area is enabled and/or at least one antioxidant in an amount that reduces the increase of oxidation index to less than 100% per 6 months and/or at least one microbicide in an amount that reduces the bacterial count of 1 million germs added per g of total mass of the formulation to less than 100 in the case of aerobic bacteria, to less than 10 in the case of enterobacteria, and to less than 1 in the case of *Pseudomonas aeruginosa* or *Staphilococcus aureus*, after a period of 4 days.

33 Claims, 8 Drawing Sheets

FOREIGN PATENT DOCUMENTS

| WO | WO 88/07362 | 10/1988 |
| --- | --- | --- |
| WO | WO 90/09782 | 9/1990 |
| WO | WO 91/04013 | 4/1991 |
| WO | 9203122 | 3/1992 |
| WO | WO 92/05771 | 4/1992 |
| WO | WO-92/22292 | 12/1992 |
| WO | WO 93/19736 | 10/1993 |
| WO | WO 93/19737 | 10/1993 |
| WO | WO-94/26257 | 11/1994 |
| WO | WO-95/35095 | 12/1995 |
| WO | WO-96/29999 | 10/1996 |
| WO | WO-97/21428 | 6/1997 |
| WO | WO 98/06750 | 2/1998 |
| WO | WO-98/07414 | 2/1998 |
| WO | WO 98/17255 | 4/1998 |
| WO | WO 98/30215 | 7/1998 |
| WO | WO 98/33483 | 8/1998 |
| WO | WO-00/13684 | 3/2000 |
| WO | WO-00/25822 | 5/2000 |
| WO | WO-00/38653 | 7/2000 |
| WO | WO-00/44350 | 8/2000 |
| WO | WO-00/50007 | 8/2000 |
| WO | WO-01/01963 | 1/2001 |
| WO | WO-01/12155 | 2/2001 |
| WO | WO-02/07767 A2 | 1/2002 |
| WO | WO-02/11683 | 2/2002 |

OTHER PUBLICATIONS

G. Cevc, Transfersomes, Liposomes and Other Lipid Suspensions on the Skin: Permeation Enhancement, Vesicle Penetration, and Transdermal Drug Delivery, *Crit. Rev. Ther. Drug Carrier Syst.*, 13(3&4), pp. 257-388, 1996.

A. Klibanov, et al., Activity of amphipathic poly(ethylene glycol) 5000 to prolong the circulation time of liposomes depends on the liposome size and is unfavorable for immunoliposome binding to target, *BBA*, 1062, pp. 141-148, 1991.

Benner, "The Human Body, The Wonderwork of the Human Body, Structure, Functions, Interactions, Processes and Mechanisms" Weltbild GmbH Augsburg (1995).

Serva, Feinbiochemica Fur Forschung for *Serva Feinbiochemica GmbH & Co.* (1986/1987).

Clark, J.M., Jr., "Experimental Biochemistry" Biochemistry Division, Department of Chemistry, University of Illinois, pp. 47-48.

Patel, H.M. "Liposomes as a Controlled-release System" Biomedical Society Transactions 609th Meeting, Leeds, pp. 513-516.

Fieser, L.F., et al. "Organische Chemie" *Hans Ruprecht Hensel, 2nd revised edition, Verlag Chemie GmbH, Weinheim/Bergstr* (1968).

Fluka Chemika-BioChemika Catalogue 16 (1988/89).

Roeding, J. "Liposomes and Niosomes in Pharmacy and Cosmetic State of the Art Prospects, Techniques of Visualizing Vesicular Systems, Interaction of Liposomes with the Skin" *Training Course No. 105 from May 14 to 16, 1990, MARITIM Hotel Nurnberg, Frauentorgraben 11, 8500 Nurenbwerg*.

L. Löbbecke, et al., "Effects of Short-Chain Alcohols On the Phase Behavior And Interdigitation Of Phosphatidylcholine Bilayer Membranes," *Biochimiea et Biophysica Aeta*, 1237, pp. 59-69, 1995.

R. Singh, et al., "Liposomally Encapsulated Diclofenac For Sonophoresis Induced Systemic Delivery," *J. Microencapsulation*, vol. 12, No. 2, pp. 149-154, 1995.

T. Henmi, et al., "Application of an Oily Gel Formed by Hydrogenated Soybean Phgospholipids as a Percutaneous Absorption-Type Ointment Base," *Chem. Pharm. Bull*, 42(3), pp. 651-655, 1994.

M. Foldvari, et al., "Dermal Drug Delivery by Liposome Encapsulation: Clinical and Electron Microscopic Studies," *J. Microencapsulation*, vol. 7, No. 4, pp. 479-489, 1990.

M. Foldari, "In Vitro cutaneous and Percutaneous Delivery and in Vivo Efficacy of Tetracaine from Liposomal and Conventional Vehicles," *Pharmaceutical Research*, vol. 11, No. 11, 1994.

M. Foldari, "Effect of Vehicle on Topical Liposomal Drug Delivery: Petrolatum Bases," *J. Microencapsulation*, vol. 13, No. 5, pp. 589-600, 1996.

M.E. Planas, et al., "Noninvasive Percutaneous Induction of Topical Analgesia by a New Type of Drug Carrier, and Prolongation of Local Pain Insensitivity by Anesthetic Liposomes," *Anesth. Analg.*, 75, pp. 615-621, 1992.

H. Peters, et al., "Pharmacodynamics of a Liposomal Preparation for Local Anaesthesia," *Arzneim.-Forsch./Drug Res.*, 45(II), Nr. 12, 1995.

I. Stoye, et al, "Transformation of a Liposomal Dispersion Containing Ibuprofen Lysinate and Phospholipids into Mixed Micelles—Physico-chemical Characterization and Influence on Drug Permeation through Excised Human StratumCorneum," *European Journal of Pharmaceutics and Biopharmaceutics*, 46, pp.191-200, 1998.

J. Schramlova, et al., "The Effect of an Antiphlogistic Incorporated in Liposomes on Experimentally Induced Inflammation," *Folia Biologica (Praha)*, 43, pp. 195-199, 1997.

G. Cevc, "Drug Delivery Across the Skin," Exp. Opin. Invest. Drugs, 6(12), pp. 1887-1937, 1997.

G. Cevc et al., Transfersomes-mediated transepidermal delivery improves the regio-specificity and biological activity of corticosteroids in vivo, *Journal of Controlled Release* 45 (1997) 211-226.

V.M. Knepp et al., Controlled Drug Release From a Novel Liposomal Delivery System II. Transdermal Delivery Characteristics, *Journal of Controlled Release* 12 (1990) Mar. No. 1, Amsterdam, NL, pp. 25-30.

C.E. Price, "A Review of the Factors Influencing the Penetration of Pesticides Through Plant Leaves" on I.C.I. Ltd., Plant Protection Division, Jealott's Hill Research Station, Bracknell, Berkshire RG12 6EY, U.K., pp. 237-252.

K. Karzel and R. K. Liedtke, "Mechanismen Transkutaner Resorption" on *Grandlagen.Basics*, pp. 1487-1491.

Michael Mezei, "Liposomes as a Skin Drug Delivery System" 1985 Elsevier Science Publishers B.V. (Biomedical Division), pp. 345-358.

Adrienn Gesztes and Michael Mezei,, "Topical Anesthesia of the Skin by Liposome-Encapsulated Tetracaine" on *Anesth Analg*, 1988; 67: pp. 1079-81.

A. Helenius, et al. "Solubilization of Membranes by Detergents", *Biochimica et Biophysica Acta*, 415 (1975) 29-79.

Phillip G. Green, et al., "In Vitro and In Vivo Enhancement of Skin Permeation With Oleic and Lauric Acids" on *International Journal of Pharmaceutics*, 48 (1988), pp. 103-111.

Guia M. Golden et al., "Role of Stratum Corneum Lipid Fluidity in Transdermal Drug Flux" on *Journal of Pharmaceutical Sciences*, vol. 76, No. 1, Jan. 1987, American Pharmaceutical Association, pp. 25-28.

Bruce J. Aungst et al., "Enhancement of Naloxone Penetration Through Human Skin In Vitro Using Fatty Acids, Fatty Alcohols, Surfactants, Sulfoxides and Amides" on *International Journal of Pharmaceutics*, 33 (1986) pp. 225-234.

Ronald R. Burnette et al., "Characterization of the Permselective Properties of Excised Human Skin During Lontophoresis" on *Journal of Pharmaceutical Sciences*, vol. 76, No. 10, Oct. 1987, American Pharmaceutical Association, pp. 765-773.

E.C. Katoulis et al., "Efficacy of a New Needeless Insulin Delivery System Monitoring of Blood Glucose Fluctuations and Free Insulin Levels" on *International Journal of Artificial Organs*, vol. 12, No. 5, 1989, pp. 333-338.

Ovals Siddiqui et al., "Nonparenteral Administration of Peptide and Protein Drugs" on *CRC Critical Reviews in Therapeutic Drug Carrier Systems*, vol. 3, Issue 3, pp. 195-208.

Cevc, G. et al., "Ultraflexible vesicles, Transfersomes, have an extremely low pore penetration resistance and transport therapeutic amounts of insulin across the intact mammalian skin," *Biochimica et Biophysica Acta.*, 1368 pp. 201-215 (1998).

Cevc, G., "Material Transport Across Permeability Barriers by Means of Lipid Vesicles," *Handbook of Biological Physics*, vol. 1, pp. 465-490 (1995).

Mayer, L.D. et al., "Vesicles of variables sizes produced by a rapid extrusion procedure," *Biochimica et Biophysica Acta*, 858 pp. 161-165 (1986).

Patel, H.M. et al., "Oral Administration of Insulin by Encapsulation Within Liposomes," *FEBS Letters*, 62(1):60-63 (Feb. 1976).

Schreier, H., "Liposomes—A Novel Drug Carrier, I. Phospholipids; Production and Characterization of Liposomes; II. Destiny of liposomes in vivo; use in therapy," *Pharmazie in unserer Zeit*, No. 4 (1982).

Beyer, C. et al., "Micro Emulsions" *Pharmazie in unserer Zeit*, No. 2 (1983).

Lichtenberg, D. et al., "Solubilization of Phospholipids by Detergents Structural and Kinetic Aspects," *Biochimica et Biophysica Acta*, 737 pp. 285-304 (1983).

Lasch, J. et al., "Interactions of external lipids (lipids vesicles) with the skin," *Journal of Liposome Research*, 5(3) pp. 543-569 (1995).

Berger, M., "Oral Insulin 1922-1992: The History of Continuous Ambition and Failure," Heinrich-Heine-University, Dusseldorf, Germany.

Cevc. G. et al., "The skin: a pathway for systemic treatment with patches and lipid-based agent carriers," *Advanced Drug Delivery Reviews* 18 pp. 349-378 (1996).

M.L. Jackson, et al. "Solubilization of Phosphatidylcholine Bilayers by Octyl Glucoside," *biochemistry* 1982, 21, 4576-4582.

P. Vinson, et al., "Vesicle-Micelle Transition of Phosphatidylcholine and Octyl Glucoside Elucidated by Cryo-Transmission Ele Tron Microscopy," *Biophys. J., Biophysical Society* vol. 56 Oct. 1989 669-681.

K. Edwards, et al., "Effects of Triton X-100 on Sonicated Lecithin Vesicles," *Langmuir* vol. 5, No. 2, 1989 pp. 473-478.

A. Brendzel, et al., "Effects of Lipid-Soluble Substances on the Thermotropic Properties of Liposome Filtration," *Biochimica et Biophysica Acta*, 601 (1980) 260-270.

G. Blume, et al., "Drug-Carrier and Stability Properties of the Long-Lived Lipid Vesicles, Cryptosomes, In Vitro and In Vivo," *Journal of Liposome Research*, 2(3), 355-368 (1992).

Ulmanns Encyklopadie der technischen Chemie, Autoren-und Sachregister, pp. 245-246. 4th ed.

Prof. Dr. Jurgen Falbe, et al., "Rompp Chemie Lexikon," p.3168.

Encyclopedia of Chemical Technology, Third Edition, pp. 835-836.

Kurt H. Bauer, et al., "Lehrbuch der Pharmazeutischen Technologie," p. 464, 1999.

Dr. Ursula Schoffling, Trier, "Ein Lehrbuch der Galenik Fur Theorie und Praxis," p. 459, 1998.

B. Halliwell and J. M.C. Gutteridge, "Free Radicals in Biology and Medicine," Third Edition, p. 925.

Klare S. Markley, "Fatty Acids: Their Chemistry, Properties, Production, and Uses," Second Completely Revised and Augmented Edition, Part 1, p. 703, 1960.

Klare S. Markley, "Fatty Acids: Their Chemistry, Properties, Production, and Uses," Second Completely Revised and Augmented Edition, Part 2, pp. 1473-1474, 1961.

Dr. Hermann Pardun, "Die Pflanzenlecithine: Gewinnung, Eigenschaften, Verarbeitung und Anwendung pflanzlicher Phosphatidpraparate," Verlag fur chemische Industrie H. Ziolkowsky KG, Augsburg, p. 552, 1988.

Gregory Gregoriadis, "Drug Carriers in Biology and Medicine," Academic Press, p. 361-361.

Gregor Cevc, "Phospholipids Handbook," Marcel Dekker, Inc., p. 878, 1993.

"The detection of oxidation in liposome preparations," *Biochim. biophys. Acta*, 210, pp. 486-489, 1970.

Dov Lichtenberg, "Liposomes: Preparation, Characterization, and Preservation," *Methods of Biochemical Analysis*, vol. 33, pp. 337, 359-360..

Dr. Ernst Mutscher, "Arzneimittel-wirkungen: Lehrbuch der pharmakologie und Toxikologie," 1991.

Dr. Rainer H. Muller, et al., "Pharmazeutische Technologie: Moderne Arzneiformen," 1998.

Phospholipids in Cosmetics and Pharmaceuticals, Rhone-Poulenc Rorer, Nattermann Phospolipid GMBH, p. 9/51, Apr. 1997.

H. Sucker, et al., "Pharmazeutische Technologie," pp. 644-649, 1978.

H. Sucker, et al., "Pharmazeutische Technologie," pp. 288, 293-300, 1978.

H. Sucker, et al., "Pharmazeutische Technologie," pp. 312-315, 1978.

H. Sucker, et al., "Pharmazeutische Technologie," pp. 315-320, 1978.

Ullmann's Encyclopedia of Industrial Chemistry, 4th edition, vol. 18, p. 57.

* cited by examiner

FORMULATION FOR TOPICAL NON-INVASIVE APPLICATION IN VIVO

This is a continuation of Application No. PCT/EP98/08421, filed Dec. 23, 1998.

The invention relates to formulations comprising molecular arrangements which, owing to penetrant adaptability, are capable of penetrating pores in a barrier, despite the fact that the average diameter of said pores is smaller than the average penetrant diameter. The penetrants can transport agents or else enable agent permeation through the pores after said penetrants have entered said pores. The invention especially relates to new additives to said formulations, such as consistency builders, anti-oxidants or microbicides. It further relates to the preparation and use of such formulations wherein the agent is selected from corticosteroids. Finally, it relates to a method for the preparation of all such formulations.

The efficacy of any drug action is a multiparameter function in which the instrinsic potency, the accumulation as well as the elimination kinetics of the drug all play a role. While the former is entirely determined by the chemical composition of the drug the latter two parameters are sensitive to the galenic characteristics of agent formulation and also depend on the site and rate of agent administration.

Choosing the right mode and kind of drug application is thus as important as finding the right agent—in medicine as well as in the pharmaceutical industry. For example, if an epicutaneously administered drug is incapable of getting into and/or across the skin barrier such a drug has no practical value even if it has a high intrinsic potency. The same is true for the drugs that get into the skin easily but are there eliminated too rapidly to fully develop the desired biological action. In either case an optimization of agent formulation may help. Devising an improved galenic formulation is also much faster and more inexpensive than the invention of the corresponding new chemical entity.

It is already known in the art that the addition of surfactants to a membrane built from an amphiphilic substance may modify the membrane's adaptability to the pores of a porous barrier. Moreover, it has already been suggested that this fact may be used to provide agent transport into and/or across the skin, by incorporating and/or associating the agent into/on miniature droplets surrounded by the corresponding membranes, of at least one or more layers of amphiphilic molecules or an amphiphilic carrier substance, and suspended in a suitable liquid medium. These formulations are based on self-optimizing agent carriers which can penetrate a porous barrier such as skin by the virtue of their extremely high adaptability to the pores. This is described in greater detail in our earlier applications EP 475 160 B1, PCT/EP96/04526, PCT/EP98/5539 and PCT/EP98/6750, which are incorporated herein for reference.

Although the above-cited prior art already teaches a formulation comprising highly adaptable topically administered agent carriers which are suitable to enable agent transport into and/or across barriers, such as the human skin, however, these formulations are still capable of optimization in specific galenic characteristics in order to enhance practicability in storage and use. This holds especially true where certain galenic characteristics such as formulation viskosity, chemical resistance to oxidative degradation and/or microbiological stability of the formulation are concerned.

To avoid a repeated treatment, e.g. in view of side-effects possibly evoked, and in order to achieve high local agent concentration, it is necessary to appropriately adjust the viscosity of the formulation as this goal will be reached by enlarging the application area and/or layer thickness of the applied formulation. Varying the viscosity of the formulation is thus an appropriate means to avoid a number of successive treatments or else to enable appropriately high agent concentrations.

Storage related problems most often arise through lack of chemical resistance of the formulation against oxidative degradation of its components. This will obviously not only be important during the storage of the formulation inside the vessel before the application, but also during the application on the application site, when the formulation is exposed to ambient oxygen. Any oxidative process involving formulation components may not only degrade carrier and agent molecules and therefore continuously destroy both carrier and agent properties, but may also even lead to the formation of free radicals which then will cause further chemical attack on carrier and agent molecules, and therefore lead to an accelerated degradation of the components in the formulation. Ensuring proper storage and use therefore always involves protection of the formulation against oxidative degradation of its components.

Another storage-related problem lies in the prevention of the formulation against affection with microbes, such as bacteria and fungi, as this may also lead to degradation of carrier components and associated agent. Microbiological affection will not only reduce or eliminate both penetration ability of the carrier and activity of the agent, but can moreover lead to severe side-effects during the application of the drug. Therefore the formulation should not only be prevented from microbiological affection during its storage before use of the formulation, but should also be kept without affection once the vessel has been broken for the purpose of the application of the drug.

Above mentioned problems relating to poor agent transport into and/or across the skin and further to galenic characteristics are quite common to many corticosteroidal dermatics. Mineralocorticoids and glucocorticoids (hereinafter collectively referred to by the more general term "corticosteroids") are contained in approximately one third of all dermatics which now may be sold over the counter. Corticosteroids are commonly used, for instance, for the topical treatment of inflammatory diseases, but also are widely used for systemic medication, especially in the treatment of allergy-based syndroms.

Administered doses between a few micrograms per square centimeter, for the most potent corticosteroidal agents, and up to a milligram per square centimeter for the less powerful drugs hence are quite common. Supraceding this limit reduces the efficacy of the concentration-driven drug permeation into the skin below the therapeutically accepatable level; superceding such drug amounts may result in intolerable local, or even systemic, side effects or else is simply not achievable by means of the classical galenic formulations.

For example, by raising the epidermal drug concentration one can increase the rate of drug transfer into the skin; by creating a local drug depot the problem of too rapid agent elimination may be solved. However, using a highly concentrated drug solution on the skin incurs the danger of agent precipitation on the skin and the greater likeliness of undesired side-effects. High skin irritation potential of many depot formulations, for example, is a serious obstacle for the successful therapeutic application of such medications. One of the chief reasons for this is that the currently used skin ointments or creams typically contain at least 0.1% and sometimes up to 5% of active ingredient as well as, a relative great amount of skin permeation enhancers in order to fluidize, which means to "soften" the skin which are however also very harmful to the skin. This is especially true when such drugs are used repeatedly and/or highly concentrated which often results in severe side effects, such as skin atrophy, which then enforces discontinuation of the therapy. Classical galenic formulations thus are generally lacking in potency and duration of biological functions if undesired severe side-effects evoked by a repeated treatment necessary to obtain sufficient agent concentration are to be avoided.

In view of the difficulties and problems cited hereinabove it would be desirable to have a formulation based on highly adaptable agent carriers which is more potent and can exert its desired biological function longer than similar drugs in the classical lotion or cream form, whereas severe side effects evoked by a repeated treatment can be reduced or even eliminated. It moreover is desirable to have a formulation based on highly adaptable agent carriers able to transport corticosteroidal agents into and/or across the skin wherein the viscosity of the formulation can be adjusted to enable enlarged application area and/or layer thickness, in order to avoid repetition in the treatment. It would also be very desirable if this formulation could be prevented from oxidative degradation and microbiological affection during its storage and use.

The present invention therefore aims at the solution of the above discussed problems. It especially addresses the problems with regard to storage and use of the specially optimized, highly adaptable agent carriers.

It is a further object of the present invention to overcome deficiencies of the prior art in delivering corticosteroidal formulations with regard to a well controlled trans- and/or intra-cutaneous transport of such drugs. Corticosteroidal formulations moreover are to be adjusted in viscosity, and prevented from oxidative degradation and microbiological affection.

Another object of the present invention is to provide a method for the preparation of such formulations for non-invasive applications.

Solutions to these objects in accordance with present invention are defined in the attached independent claims.

Convenient solutions with special properties are provided by the subject-matters of the subclaims.

As mentioned above the preparation and use of a formulation based on highly adaptable agent carriers have already been described in references incorporated herein. From these it is already generally known to add consistency builders and anti-oxidants to some such formulations, (cf. e.g. PCT/EP96/04526; Claim 18). However, this teaching is a general rule without any practical value, as it obviously lacks any specification for the use. This holds especially true, for instance, for the addition of a consistency builder which enables the formulation to be adjusted to the intended dose of the drug. This addition can obviously not be effected by a simple trial-and-error procedure, or accidentally, by the skilled person, since final drug action is essentially concerned. It is moreover essentiell to appropriately select type and amount of the added anti-oxidant or microbicide, as this obviously affects storage and use of the formulation.

It is known from prior art to use corticosteroids as the agent associated with highly adaptable agent carriers (cf. PCT/EP96/04526; Claim 15; PCT/EP91/01596 Examples 173–175). But, as for said additives, this disclosure provides no more than a general rule, to add said agent to said agent carriers without any further specification, as is however considered essentiell for the application of the drug. Consequently said prior art only generally teaches the use of corticosteroids as a test agent for the evaluation of pore penetration rate, rather than teaching the preparation of a usable dermatics product based on highly adaptable agent carriers containing corticosteroids. This is indicated by the total amount of hydrocortisone which is to be incorporated in the highly adaptable carrier (examples 173–175 of PCT/EP91/01596: 10 Mikrograms per about 100 mg dry weight of agent carrier). The very low relative proportion of about 0,1 per mille of hydrocortisone based on the total dry weight of formulation is far away from any therapeutically useful drug concentration and also far away from any corticosteroid concentration given in this application.

Figure 1:
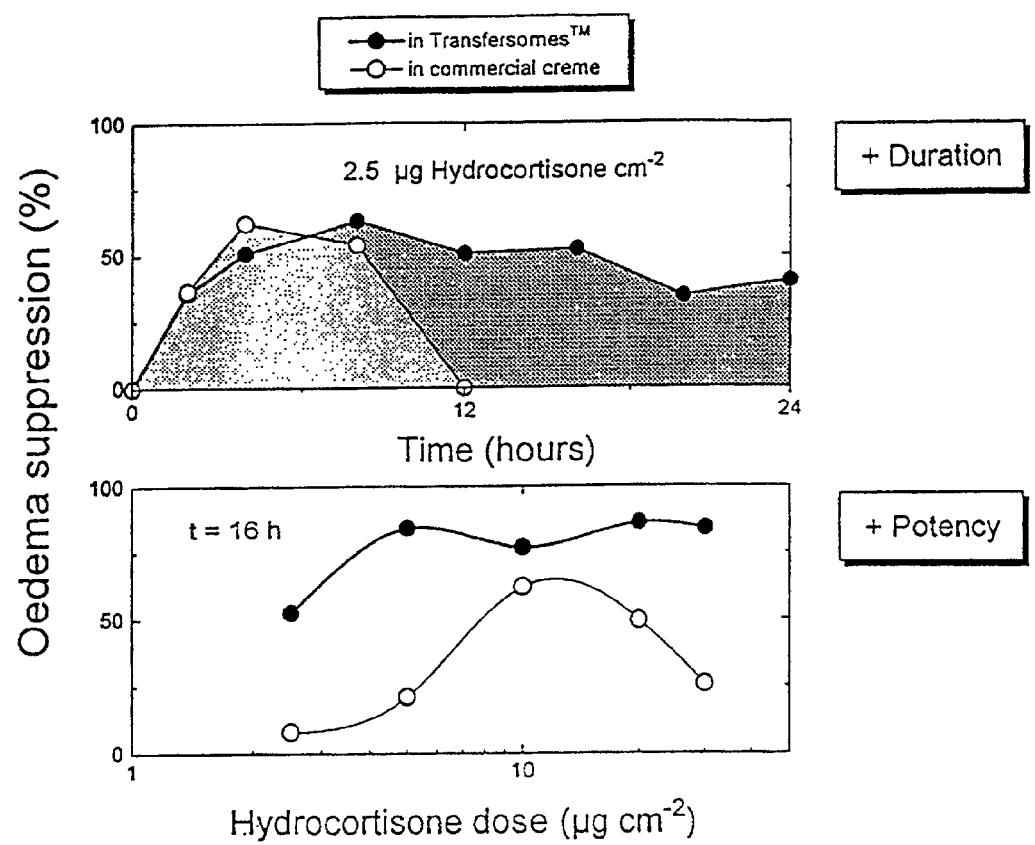
FIG. 1 shows the results of biological experiments in which oedema-suppression activity of hydrocortisone in a commercial reference creme (open symbols) was tested against the same amount of identical drug in highly deformable lipid vesicles (Transfersomes) (closed symbols) in mice. The upper panel contains time-dependence ("pharmacodynamic") data, whereas the lower panel gives the dose dependency measured 16 h after the drug application. Data points give the mean values for 3–4 animals.

Furthermore, in general, both topical non-systemic administration, and substantially systemic administration of corticosteroidal dermatics is accompanied by the problem that the more gentle acting agents, like hydrocortisone, only exhibit a rather short and week activity, whereas the more recently developped related agents, such as prednicarbat- or triamcinolone-derivatives are more potent and also act longer, but are also more harmful to the body, as they can evoke severe side-effects if they are applied highly concentrated and/or repeatedly.

In contrast to this, topical corticosteroid delivery mediated by highly adaptable agent carriers can be varied systematically whereby severe side-effects are dramatically reduced or even avoided. Depending on the precise application conditions and carrier design, between 100% and less than 5% of the locally administered drug can be deposited into the outermost skin region. Low area-dose favors drug retention in the skin, while larger amounts of a drug shift the distribution towards systemic circulation. It is possible to reach therapeutically meaningful drug concentrations in the blood after a single epicutaneous administration of corticosteroids by said carriers, while one can also keep blood level below a few per cent.

Unexpectedly, employment of such highly adaptable agent carriers together with an agent selected from corticosteroids provides biologically efficient product at unprecedent small doses per area. As is shown further below, all tested corticosteroids thus gained in potency (by the factor of 2 to 10) and in duration of action (by up to 5-fold) when they were administered on the intact skin by means of highly adaptable agent carriers. In contrast to prior art, ointments and creams containing corticosteroids, minute amounts of corticosteroids in highly adaptable agent carriers, consequently, suffice for good biological drug action.

Generally, material abrasion from the surface shortens the therapeutic effect in a conventional cream or lotion. It is another advantage of the present invention that such problems are not obversed with the formulations based on highly adaptable agent carriers which thus exert a much longer biological action than standard correponding medications. This is due to the fact that such highly adaptable agent carriers generate a drug depot in the viable skin portions, rather than on the skin surface.

It is a characteristic feature of the present invention, that a formulation comprising molecular arrangements capable of penetrating pores in a barrier, owing to penetrant adaptability, despite the fact that the average diameter of said pores is smaller than the average penetrant diameter, provided that the penetrants can transport agents or else enable agent permeation through the pores after penetrants have entered pores comprises at least one consistency builder in an amount that increases the formulation viscosity above that of the non-thickened corresponding formulation to maximally 5 Nm/s so that spreading over, and retention at, the application area is enabled and/or at least one antioxidant in an amount that reduces the increase of oxidation index to less than 100% per 6 months and/or at least one microbicide in an amount that reduces the bacterial count of 1 million germs added per g of total mass of the formulation to less than 100 in the case of aerobic bacteria, to less than 10 in the case of entero-bacteria, and to less than 1 in the case of *Pseudomonas aeruginosa* or *Staphilococcus aureus*, after a period of 4 days. It thus is possible to prolong storage and use of the formulation and to advantageously increase practicability of the formulation.

It then is preferred if said at least one consistency buildner is added in an amount that increases the formulation viscosity to up to 1 Nm/s and more preferably to up to 0.2 Nm/s.

It also is preferred if said at least one antioxidant is added in an amount that reduces the increase of oxidation index to less than 100% per 12 months and more preferably to less than 50% per 12 months.

For a formulation comprising soy bean phosphatidylcholine as the main degrading species, the increase of the oxidation index is reduced to less than 0.45 units, preferably to less than 0.22 units and even more preferably to less than 0.1 units, per 12 month.

In preferred embodiments of the invention said at least one microbicide is added in an amount that reduces the bacterial count of 1 million germs added per g of total mass of the formulation to less than 100 in the case of aerobic bacteria, to less than 10 in the case of entero-bacteria, and to less than 1 in the case of *Pseudomonas aeruginosa* or *Staphilococcus aureus*, after a period of 3 days, and more preferably after a period of 1 day.

It is preferred if that anti-oxidant is selected from synthetic phenolic antioxidants, such as butylated hydroxyanisol (BHA), butylated hydroxytoluene (BHT) and di-tert-butylphenol (LY178002, LY256548, HWA-131, BF-389, CI-986, PD-127443, E-5119, BI-L-239XX, etc.), tertiary butylhydroquinone (TBHQ), propyl gallate (PG), 1-O-hexyl-2,3,5-trimethylhydroquinone (HTHQ); aromatic amines (diphenylamine, p-alkylthio-o-anisidine, ethylenediamine derivatives, carbazol, tetrahydroindenoindol); phenols and phenolic acids (guaiacol, hydroquinone, vanillin, gallic acids and their esters, protocatechuic acid, quinic acid, syringic acid, ellagic acid, salicylic acid, nordihydroguaiaretic acid (NDGA), eugenol); tocopherols (including tocopherols (alpha, beta, gamma, delta) and their derivatives, such as tocopheryl-acylate (e.g. -acetate, -laurate, myristate, -palmitate, -oleate, -linoleate, etc., or an y other suitable tocopheryl-lipoate), tocopheryl-POE-succinate; trolox and corresponding amide and thiocarboxamide analogues; ascorbic acid and its salts, isoascorbate, (2 or 3 or 6)-o-alkylascorbic acids, ascorbyl esters (e.g. 6-o-lauroyl, myristoyl, palmitoyl-, oleoyl, or linoleoyl-L-ascorbic acid, etc.). It may also be advantageous to use various drugs interfering with oxidation, including but not limited to non-steroidal anti-inflammatory agents (NSAIDs, such as indomethacine, diclofenac, mefenamic acid, flufenamic acid, phenylbutazone, oxyphenbutazone acetylsalicylic acid, naproxen, diflunisal, ibuprofene, ketoprofene, piroxicam, penicillamine, penicillamine disulphide, primaquine, quinacrine, chloroquine, hydroxychloroquine, azathioprine, phenobarbital, acetaminephen); aminosalicylic acids and derivatives; methotrexate, probucol, antiarrhythmics (amiodarone, aprindine, asocainol), ambroxol, tamoxifene, b-hydroxytamoxifene; calcium antagonists (nifedipine, nisoldipine, nimodipine, nicardipine, nilvadipine), beta-receptor blockers (atenolol, propranolol, nebivolol); also useful are the preferentially oxidised compounds, such as sodium bisulphite, sodium metabisulphite, thiourea; chellating agents, such as EDTA, GDTA, desferral; miscellaneous endogenous defence systems, such as transferrin, lactoferrin, ferritin, cearuloplasmin, haptoglobion, heamopexin, albumin, glucose, ubiquinol-10); enzymatic antioxidants, such as superoxide dismutase and metal complexes with a similar activity, including catalase, glutathione peroxidase, and less complex molecules, such as beta-carotene, bilirubin, uric acid; flavonoids (flavones, flavonols, flavonones, flavanonals, chacones, anthocyanins), N-acetylcystein, mesna, glutathione, thiohistidine derivatives, triazoles; tannines, cinnamic acid, hydroxycinnamatic acids and their esters (coumaric acids and esters, caffeic acid and their esters, ferulic acid, (iso-) chlorogenic acid, sinapic acid); spice extracts (e.g. from clove, cinnamon, sage, rosemary, mace, oregano, allspice, nutmeg); carnosic acid, carnosol, carsolic acid; rosmarinic acid, rosmaridiphenol, gentisic acid, ferulic acid; oat flour extracts, such as avenanthramide 1 and 2; thioethers, dithioethers, sulphoxides, tetralkylthiuram disulphides; phytic acid, steroid derivatives (e.g. U74006F); tryptophan metabolites (e.g. 3-hydroxykynurenine, 3-hydroxyanthranilic acid), and organochalcogenides.

Especially, a preferred concentration of BHA or BHT is between 0.001 and 2 w-%, more preferably is between 0.0025 and 0.2 w-%, and most preferably is between 0.005 and 0.02 w-%, of TBHQ and PG is between 0.001 and 2 w-%, more preferably is between 0.005 and 0.2 w-%, and most preferably is between 0.01 and 0.02 w-%, of tocopherols is between 0.005 and 5 w-%, more preferably is between 0.01 and 0.5 w-%, and most preferably is between 0.05 and 0.075 w-%, of ascorbic acid esters is between 0.001 and 5, more preferably is between 0.005 and 0.5, and most preferably is between 0.01 and 0.15 w-%, of ascorbic acid is between 0.001 and 5, more preferably is between 0.005 and 0.5 w-%, and most preferably is between 0.01 and 0.1 w-%, of sodium bisulphite or sodium metabisulphite is between 0.001 and 5, more preferably is between 0.005 and 0.5 w-%, and most preferably is between 0.01–0.15 w-%, of thiourea is between 0.0001 and 2 w-%, more preferably is between 0.0005 and 0.2, and most preferably is between 0.001–0.01 w-%, most typically 0.005 w-%, of cysteine is between 0.01 and 5, more preferably is between 0.05 and 2 w-%, and most preferably is between 0.1 and 1.0 w-%, most typically 0.5 w-%, of monothioglycerol is between 0.01 and 5 w-%, more preferably is between 0.05 and 2 w-%, and most preferably is between 0.1–1.0 w-%, most typically 0.5 w-%, of NDGA is between 0.0005–2 w-%, more preferably is between 0.001–0.2 w-%, and most preferably is between 0.005–0.02 w-%, most typically 0.01 w-%, of glutathione is between 0.005 and 5 w-%, more preferably is between 0.01 and 0.5 w-%, and most preferably is between 0.05 and 0.2 w-%, most typically 0.1 w-%, of EDTA is between 0.001 and 5 w-%, even more preferably is between 0.005 and 0.5 w-%, and most preferably is between 0.01 and 0.2 w-%, most typically between 0.05 and 0.975 w-%, of citric acid is between 0.001 and 5 w-%, even more preferably is between 0.005 and 3 w-%, and most preferably is between 0.01-0.2, most typically between 0.3 and 2 w-%.

In preferred embodiments of the invention, the microbicide is selected from short chain alcohols, including ethyl and isopropyl alcohol, chlorbutanol, benzyl alcohol, chlorbenzyl alcohol, dichlorbenzylalcohol, hexachlorophene; phenolic compounds, such as cresol, 4-chloro-m-cresol, p-chloro-m-xylenol, dichlorophene, hexachlorophene, povidon-iodine; parabenes, especially alkyl-parabenes, such as methyl-, ethyl-, propyl-, or butyl-paraben, benzyl paraben; acids, such as sorbic acid, benzoic acid and their salts; quaternary ammonium compounds, such as alkonium salts, e.g. a bromide, benzalkonium salts, such as a chloride or a bromide, cetrimonium salts, e.g. a bromide, phenoalkecinium salts, such as phenododecinium bromide, cetylpyridinium chloride and other salts; furthermore, mercurial compounds, such as phenylmercuric acetate, borate, or nitrate, thiomersal, chlorhexidine or its gluconate, or any antibiotically active compounds of biological origin, or any suitable mixture thereof.

In especially preferrred embodiments, the bulk concentration of short chain alcohols in the case of ethyl, propyl, butyl or benzyl alcohol preferably is up to 10 w %, more preferably is up to 5 w-%, and most preferably is in the range between 0.5–3 w-%, and the bulk concentration of chlorobutanol preferably is in the range between 0.3–0.6 w-%; furthermore, the preferred bulk concentration of parabenes is in the range between 0.05–0.2 w-%, in the case of methyl paraben, and is in the range between 0.002–0.02 w-%, in the case of propyl paraben; bulk concentration of sorbic acid preferably is in the range between 0.05–0.2 w-%, and in the case of benzoic acid preferably is in the range between 0.1–0.5 w-%; bulk concentration of phenols, triclosan, is preferably in the range between 0.1–0.3 w-%, and bulk concentration of chlorhexidine preferably is in the range between 0.01–0.05 w-%.

It further is preferred if that consistency builder is selected from pharmaceutically acceptable hydrophilic polymers, such as partially etherified cellulose derivatives, comprising carboxymethyl-, hydroxyethyl-, hydroxypropyl-, hydroxypropylmethyl- or methyl-cellulose; completely synthetic hydrophilic polymers comprising polyacrylates, polymethacrylates, poly(hydroxyethyl)-, poly(hydroxypropyl)-, poly(hydroxypropylmethyl)methacrylate, polyacrylonitrile, methallyl-sulphonate, polyethylenes, polyoxiethylenes, polyethylene glycols, polyethylene glycol-lactide, polyethylene glycol-diacrylate, polyvinylpyrrolidone, polyvinyl alcohols, poly(propylmethacrylamide), poly(propylene fumarate-co-ethylene glycol), poloxamers, polyaspartamide, (hydrazine cross-linked) hyaluronic acid, silicone; natural gums comprising alginates, carrageenan, guar-gum, gelatine, tragacanth, (amidated) pectin, xanthan, chitosan collagen, agarose; mixtures and further derivatives or co-polymers thereof and/or other pharmaceutically, or at least biologically, acceptable polymers. In especially, the polymer weight fractions preferably are in the range between 0.05% and 10%, more preferably are in the range between 0.1% and 5%, even more preferably are in the range between 0.25% and 3.5% and most preferably are in the range between 0.5% and 2%.

It has been found that viscosity is best suited if the consistency builder is added in an amount that increases the formulation viscosity above that of the non-thickened corresponding formulation, preferably to up to 1 Nm/s and even more preferably to up to 0.2 Nm/s.

In another aspect of the invention, a formulation comprising molecular arrangements capable of penetrating pores in a barrier, owing to penetrant adaptability, despite the fact that the average diameter of said pores is smaller than the average penetrant diameter, provided that the penetrants can transport agents or else enable agent permeation through the pores after penetrants have entered pores, the agents associated with said penetrants being glucocorticoids or mineralocorticosteroids (corticosteroids), is characterised in that the relative content of corticosteroids is above 0.1 weight-%, relative to total dry mass of the formulation. It then is preferred if at least one consistency builder and/or at least one anti-oxidant and/or at least one microbicide, as described herein, is added to the formulation.

That corticosteroid is preferably selected from alcloneta-sone dipropionate, amcinonide, beclomethasone dipropionate, betamethasone, betamethasone 17-valerate, betamethasone 17,21-divalerate, betamethasone 21-acetate, betamethasone 21-buytrate, betamethasone 21-propionate, betamethasone 21-valerate, betamethasone benzoate, betamethasone dipropionate, betamethasone valerate, budesonide, clobetasol propionate, clobetasone butyrate, cortexolone, corticosterone, cortisone, cortisone 17-acetate, 21-deoxybetamethasone, 21-deoxybetamethasone 17-propionate, deoxycorticosterone, desonide, desoxymethasone, dexamethasone, diflorasone diacetate, diflucortolone valerate, fluclorolone acetonide, flumethasone pivalate, fluocinolone acetonide, fluocinonide, fluocortin butyl, fluocortolone, 9-alpha-fluorocortisone, 9-alpha-fluorohydrocortisone, 9-alpha-fluoroprednisolone, fluprednidene acetate, flurandrenolone, halcinonide, hydrocortisone, hydrocortisone 17-acetate, hydrocortisone 17-butyrate, hydrocortisone 17-propionate, hydro cortisone 17-valerate, hydrocortisone 21-acetate, hydrocortisone 21-butyrate, hydrocortisone 21-propionate, hydrocortisone 21-valerate, 17-alpha-hydroxyprogesterone, methylprednisolone acetate, mometasone furoate, prednisolone, prednisone, prednisone 17-acetate, prednisone 17-valerate, progesterone, triamncinolone, triamcinolone acetonide.

In a specific embodiment of the invention the penetrants are suspended or dispersed in a polar liquid in the form of fluid droplets surrounded by a membrane-like coating of one or several layers, said coating comprising at least two kinds or forms of amphiphilic substances with a tendency to aggregate, provided that said at least two substances differ by at least a factor of 10 in solubility in said liquid or else that said substances when in the form of homo-aggregates, for the more soluble substance, or of hetero-aggregates, for any combination of both said substances, have a preferred average diameter smaller than the diameter of the homo-aggregates containing merely the less soluble substance; or else provided that the presence of the more soluble substance lowers the average elastic energy of the membrane-like coating in the vicinity of thermal energy.

It then is preferred that the more soluble substance tends to solubilise the droplet and the content of such substance is up to 99 mol-% of solubilising concentration or else corresponds to up to 99 mol-% of the saturating concentration in the unsolubilised droplet, whichever is higher. It can be an advantage if the content of the more soluble substance is below 50%, especially below 40% and most preferably below 30%, of the respective solubilising concentration of said substance. It also is often advantageous if the content of the more soluble substance is below 80%, preferably below 65% and most preferably below 50% of the saturation concentration of said substance in the droplet.

In many highly preferred embodiments of the invention, the less soluble amongst the aggregating substances is a lipid or lipid-like material, especially a polar lipid, whereas the substance which is more soluble in the suspending liquid and which increases the droplet adaptability belongs to the class of surfactants or else has surfactant-like properties. A specific embodiment of the invention is prepared from a lipid or lipid-like material (which may be a lipid or a lipoid from a biological source or a corresponding synthetic lipid or any of its modifications), said lipid preferably belonging to the class of pure phospholipids corresponding to the general formula

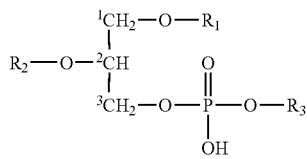

where $R_1$ and $R_2$ is an aliphatic chain, typically a $C_{10-20}$-acyl, or -alkyl or partly unsaturated fatty acid residue, in particular an oleoyl-, palmitoeloyl-, elaidoyl-, linoleyl-, linolenyl-, linolenoyl-, arachidoyl-, vaccinyl-, lauroyl-, myristoyl-, palmitoyl-, or stearoyl chain; and where $R_3$ is hydrogen, 2-trimethylamino-1-ethyl, 2-amino-1-ethyl, $C_{1-4}$-alkyl, $C_{1-5}$-alkyl substituted with carboxy, $C_{2-5}$-alkyl substituted with hydroxy, $C_{2-5}$-alkyl substituted with carboxy and hydroxy, or $C_{2-5}$-alkyl substituted with carboxy and amino, inositol, sphingosine, or salts of said substances, said lipid comprising also glycerides, isoprenoid lipids, steroids, sterines or sterols, of sulphur- or carbohydrate-containing lipids, or any other bilayer forming lipids, in particular half-protonated fluid fatty acids. Preferably, said lipid is selected from the group comprising phosphatidylcholines, phosphatidylethanolamines, phosphatidylglycerols, phosphatidylinositols, phosphatidic acids, phosphatidylserines, sphingomyelins and other sphingophospholipids, glycosphingolipids (including cerebrosides, ceramidepolyhexosides, sulphatides, sphingoplasmalogens), gangliosides and other glycolipids or synthetic lipids, in particular with corresponding sphingosine derivatives, or any other glycolipids, whereby two similar or different chains can be ester-groups-linked to the backbone (as in diacyl and dialkenoyl compound) or be attached to the backbone with ether bonds, as in dialkyl-lipids.

It is preferred if the surfactant or surfactant-like material is a nonionic, a zwitterionic, an anionic or a cationic surfactant, especially a fatty-acid or -alcohol, an alkyl-tri/di/methyl-ammonium salt, an alkylsulphate salt, a monovalent salt of cholate, deoxycholate, glycocholate, glycodeoxycholate, taurodeoxycholate, taurocholate, etc., an acyl- or alkanoyl-dimethyl-aminoxide, esp. a dodecyl- dimethyl-aminoxide, an alkyl-or alkanoyl-N-methylglucamide, N-alkyl-N,N-dimethylglycine, 3-(acyldimethylammonio)-alkanesulphonate, N-acyl-sulphobetaine, a polyethylene-glycol-octylphenyl ether, esp. a nonaethylene-glycol-octylphenyl ether, a polyethylene-acyl ether, esp. a nonaethylen-dodecyl ether, a polyethylene-glycol-isoacyl ether, esp. a octaethylene-glycol-isotridecyl ether, polyethylene-acyl ether, esp. octaethylenedodecyl ether, polyethylene-glycol-sorbitane-acyl ester, such as polyethylenglykol-20-monolaurate (Tween 20) or polyethylenglykol-20-sorbitan-monooleate (Tween 80), a polyhydroxy-ethylene-acyl ether, esp. polyhydroxyethylene-lauryl, -myristoyl, -cetylstearyl, or -oleoyl ether, as in polyhydroxyethylene-4 or 6 or 8 or 10 or 12, etc., -lauryl ether (as in Brij series), or in the corresponding ester, e.g. of polyhydroxyethylen-8-stearate (Myrj 45), -laurate or -oleate type, or in polyethoxylated castor oil 40, a sorbitane-monoalkylate (e.g. in Arlacel or Span), esp. sorbitane-monolaurate, an acyl- or alkanoyl-N-methylglucamide, esp. in or decanoyl- or dodecanoyl-N-methylglucamide, an alkyl-sulphate (salt), e.g. in lauryl- or oleoyl-sulphate, sodium deoxycholate, sodium glycodeoxycholate, sodium oleate, sodium taurate, a fatty acid salt, such as sodium elaidate, sodium linoleate, sodium laurate, a lysophospholipid, such as n-octadecylene(=oleoyl)-glycerophosphatidic acid, -phosphorylglycerol, or -phosphorylserine, n-acyl-, e.g. lauryl or oleoyl-glycero-phosphatidic acid, -phosphorylglycerol, or -phosphorylserine, n-tetradecyl-glycero-phosphatidic acid, -phosphorylglycerol, or -phosphorylserine, a corresponding palmitoeloyl-, elaidoyl-, vaccenyl-lysophospholipid or a corresponding short-chain phospholipid, or else a surface-active polypeptide.

Penetration rate of agent carriers is often maximized if the average penetrant diameter is chosen to be between 30 nm and 500 nm, preferably between 40 nm and 250 nm, even more preferably between 50 nm and 200 nm and most preferably between 60 nm and 150 nm.

Pore penetration rate of agent carriers is often optimized in terms of the relative ratio between penetrant and pore size, if the average diameter of the penetrant is 2 to 25 times bigger than the average diameter of the pores in the barrier, preferably between 2.25 and 15 times bigger, even more preferably between 2.5 and 8 times bigger and most preferably between 3 and 6 times bigger than said average pore diameter.

Specific preferred embodiments of the invention are characterized by the fact, that the dry weight of all carrier droplets in a formulation for the use on human or animal skin is 0.01 weight-% (w-%) to 40 w-% of total formulation mass, in particular between 0.1 w-% and 30 w-%, particularly preferably between 0.5 w-% and 20 w-%, and most preferably between 1 w-% and 10 w-%.

If the formulation is to be applied on human or animal mucosa the dry weight of all carrier droplets in a formulation is advantageously chosen to be in the range between 0.0001 w-% and 30 w-% of total formulation mass.

For the preparation of a formulation it is preferred if the pH of the carrier suspension is between 4 and 10, preferably between 5 and 9, and even more often up to 8.5, as required in order to maximise the stability of formulation, depending on the pH of the carrier suspension.

A method for the preparation of a formulation for non-invasive application in vivo according to the invention comprises the use of at least one amphiphilic substance, at least one polar fluid, at least one edge-active substance or surfactant, at least one corticosteroid in an amount of more than 0.1 w-% based on total dry mass of the formulation and, in case, other customary ingredients, which together form said formulation.

It then is preferred if at least one edge-active substance or surfactant, at least one amphiphilic substance, at least one hydrophilic fluid and the agent are dissolved to form a solution and, if required, are mixed separately, the resulting (partial) mixtures or solutions then being combined to subsequently induce, preferably by action of mechanical energy, such as shaking, stirring, vibrating, homogenising, ultrasonication, shear, freezing and thawing, or filtration using convenient driving pressure, the formation of penetrants that associate with and/or incorporate the agent.

It is advantageous if said amphiphilic substances are either used as such, or dissolved in a physiologically compatible polar fluid, which may be water or miscible with water, or in a solvation-mediating agent, together with a polar solution.

It further is preferred that said amphiphilic substances are dissolved in highly volatile alcohols, especially ethanol, or in other pharmaceutically acceptable organic solvents, which are then removed, esp. by evaporation, prior to making the final preparation.

It may also be advantageous if said polar solution contains at least one edge-active substance or surfactant.

For the preparation of a formulation according to the invention it further is preferred, that the formation of said penetrants is induced by the addition of the required substances into a fluid phase, evaporation from a reverse phase, by injection or dialysis, if necessary under the influence of mechanical stress, such as shaking, stirring, especially high velocity stirring, vibrating, homogenising, ultrasonication, shearing, freezing and thawing, or filtration using convenient, especially low (1 MPa) or intermediate (up to 10 MPa), driving pressure.

It then is convenient if the formation of said penetrants is induced by filtration, the filtering material having pores sizes between 0.01 μm and 0.8 μm, preferably between 0.02 μm and 0.3 μm, and most preferably between 0.05 μm and 0.15 μm, whereby several filters may be used sequentially or in parallel.

Furthermore, it is preferred if said agents and penetrants are made to associate, at least partly, after the formation of said penetrants, e.g. after injecting a solution of the drug in a pharmaceutically acceptable fluid, such as ethanol, 1- and 2-propanol, benzyl alcohol, propylene glycol, polyethylene glycol (molecular weight: 200–400 D) or glycerol into the suspending medium, said penetrants being formed previously, using the corresponding or some other suitable manufacturing method, or simultaneously with the drug injection, if required using a co-solution of the drug and, at least some, penetrant ingredients.

It may be advantageous if the penetrants, with which the agent molecules are associated and/or into which the agent molecules are incorporated, are prepared just before the application of the formulation, if convenient from a suitable concentrate or a lyophylisate.

It is preferred if the content of corticosteroids is between 0.1 relative weight % (rw-%) and 20 rw-%, more preferably between 0.25 rw-% and 10 rw-% and even more preferably between 0.5 rw-% and 5 rw-% with regard to total penetrant dry mass.

It then is preferred if said corticosteroid is triamcinolone or one of its derivatives, such as acetonide, the relative content thereof is below 2 w-%, relative to total dry mass of the drug-loaded carriers, even more preferably is below 1 w-% and most typically is below 0.5 w-%.

It also is preferred if the corticosteroid is hydrocortisone or one of its derivatives, the relative content thereof is below 20 w-%, relative to total dry mass of the drug-loaded carriers, even more preferably is below 12.5 w-% and most typically is below 5 w-%.

Further, it is preferred if said corticosteroid is dexamethasone or one of its derivatives, the relative content thereof is below 15 w-%, relative to total dry mass of the drug-loaded carriers, even more preferably is below 10 w-% and most typically is below 5 w-%.

It equally is preferred if said corticosteroid is clobetasol or one of its derivatives, such as propionate, the relative content thereof is below 15 w-%, relative to total dry mass of the drug-loaded carriers, even more preferably is below 10 w-% and most typically is below 5 w-%.

It is a preferred feature of the invention that the content of said corticosteroid is below the saturation maximum, defined as the point at which the corticosteroid begins to crystallise in or outside the carrier, such maximum depending on interactions between the amphiphilic molecules comprising the carrier and the agent molecules and frequently being reflected in the membrane/ or oil/water partition coefficient difference for the main carrier component and said corticosteroid or else relates to the mismatch in molecular size between the carrier and corticosteroid molecules, the drugs with a lower compatibility typically having lower saturation values.

It may be advantageous if in order to speed up drug action a permeation enhancer is added, which preferably is selected from 1-acyl-azacycloheptan-2-ones (azones), 1-acyl-glucosides, 1-acyl-polyoxyethylenes, 1-acyl-saccharides, 2-n-acyl-cyclohexanones, 2-n-acyl-1,3-dioxolanes (SEPA), 1,2,3-triacyl-glycerols, 1-alkanols, 1-alkanoic acids, 1-alkyl-acetates, 1-alkyl-amines, 1-alkyl-n-alkyl-polyoxyethylenes, 1-alkyl-alkylates, n-alkyl-beta-D-thioglucosides, 1-alkylglycerides, 1-alkyl-propyleneglycols, 1-alkyl-polyoxyethylenes, (1-alkyl-)2-pyrrolidones, alkyl-acetoacetates, alkylene-glycols, alkyl-methyl-sulphoxides (alkyl-DMSO), alkyl-propionates, alkyl-sulphates, diacyl-succinates, diacyl-N,N-dimethylaminoacetates (DDAA), diacyl-N,N-dimethylaminoisopropionates (DDAIP), phenyl-alkyl-amines.

This addition of permeation enhancers is not comparable to the addition of permeation enhancers as already effected in classical galenic preparations, such as ointments and lotions, as in the art, the permeation enhancers are solely added for the purpose of fluidization of the skin. In the present case the permeation enhancers are added to speed up drug action which is to speed up distribution between agent carrier and surroundings. This content of permeation enhancer is not suited to substantially fluidize skin in order to increase the pore penetration rate of agent carriers and therefore is inherently different from prior art.

It then is preferred if the bulk concentration range of the preferably used enhancers is up to and around 5% for 1-capryl-propylene glycol, 6–10% for 1-[2-(decylthio)ethyl]azacyclopentan-2-one (=HPE-101), <10% for 1-dodecanol, <10% for 1-dodecyl-azacycloheptan-2-one (=azone), in the range of 10% for 2-n-nonyl-1,3-dioxolane (SEPA), <10% for 2-n-octylcyclohexanone, up to, and preferably around, up to 20% for DMSO, up to, and preferably between 5% and 40% for ethanol, in the range of 10% or higher for ethylene glycol, up to 30% for ethyl acetate, 5–50% for glycerol, up to 75% for isopropanol, 1–20% for isopropyl myristate, between 1 and, preferably, 20% for oleic acid and oleyl-alcohol, of the order of around 1% for oleyl-polyoxyethylene-ether, at least 10% for propylene glycol.

The caveat pertaining to these ranges is that the relative and absolute potency of various skin permeation enhancers differs, which makes absolute comparisons difficult. In principle, it is the concentration of an enhancer in the skin which determines the enhancement success. However, it is the nominal enhancer concentration on the skin which typically is considered or is quoted in the literature. The two values often differ by several orders of magnitude, are sensitive to drug-enhancer association, and also may vary with the application conditions. Too small enhancer reservoir on the surface, for example, in the case of a fast enhancer diffusion across the skin or evaporation, leads to substance depletion. It also changes the final system properties.

It is a preferred feature of the invention that said corticosteroid is added in an amount which enables the formulation to be applied corresponding to an area dose, as expressed by the total dry mass of penetrant applied per unit area, of between 0.1 mg $cm^{-2}$ and 15 mg $cm^{-2}$, more preferably between 0.5 mg $cm^{-2}$ and 10 mg $cm^{-2}$, particularly preferably between 0.75 mg $cm^{-2}$ and 5 mg $cm^{-2}$ and most preferably between 1 mg $cm^{-2}$ and 2.5 mg $cm^{-2}$, if said corticosteroid is desired to exert a therapeutic effect in the deep subcutaneous, e.g. muscle or joints, tissue or else in the remote tissues, including the whole body.

It is another preferred feature of the invention that said corticosteroid is added in an amount which enables the formulation to be applied with an area dose, as expressed by the total dry mass of penetrant applied per unit area, of 1 between μg $cm^{-2}$ and 250 μg $cm^{-2}$, more preferably between 2.5 and 100 μg $cm^{-2}$, even more preferably between 5 μg $cm^{-2}$ and 50 μg $cm^{-2}$ and most preferably between 7.5 μg $cm^{-2}$ and 20 μg $cm^{-2}$, if said corticosteroid is desired to exert a mainly local, that is, superficial, rather than systemic therapeutic effect.

It is preferred if consistency and, if necessary other characteristics of the formulation are appropriately selected to enable spraying, smearing, rolling or sponging of the formulation on the application area in particular by using a sprayer, spender, roller or sponge, as appropriate.

It is another preferred feature of the invention that for non-invasive application of corticosteroids by means of said penetrants according to the invention the area dose, as expressed by the total dry mass of penetrant applied per unit area, is selected to be between 0.1 mg $cm^{-2}$ and 15 mg $cm^{-2}$, preferably between 0.5 mg $cm^{-2}$ and 10 mg $cm^{-2}$, particularly preferably between 0.75 mg $cm^{-2}$ and 5 mg $cm^{-2}$ and most preferably between 1 mg $cm^{-2}$ and 2.5 mg $cm^{-2}$, if said corticosteroid is desired to exert a substantial therapeutic effect in the deep subcutaneous, e.g. muscle or joints, tissue or else in the remote tissues, including the whole body.

It otherwise is preferred if for non-invasive application of corticosteroids by means of penetrants according to the invention the area-dose, as expressed by the total dry mass of penetrants applied per unit area, is chosen to be between 1 μg $cm^{-2}$ and 250 μg $cm^{-2}$, preferably between 2.5 μg $cm^{-2}$ and 100 μg $cm^{-2}$, more preferably between 5 μg $cm^{-2}$ and 50 μg $cm^{-2}$ and most preferably between 7.5 μg $cm^{-2}$ and 20 μg $cm^{-2}$, to achieve mainly local, that is, superficial, rather than systemic effect of the drug.

It may be advantageous if non-invasive application of corticosteroids associated with or encapsulated into penetrants according to the invention is effected by spraying, smearing, rolling or sponging on the application area in particular by using a sprayer, spender, roller or sponge, as appropriate.

A preferred use of a formulation in accordance with the invention is for the treatment of inflammatory disease, dermatosis, kidney or liver failure, adrenal insufficiency, aspiration syndrome, Behcet syndrome, bites and stings, blood disorders, such as cold-haemagglutinin disease, haemolytic anemia, hypereosinophilia, hypoplastic anemia, macroglobulinaemia, trombocytopenic purpura, furthermore, for the management of bone disorders, cerebral oedema, Cogan's syndrome, congenital adrenal hyperplasia, connective tissue disorders, such as lichen, lupus erythematosus, polymyalgia rheumatica, polymyositis and dermatomyositis, epilepsy, eye disorders, such as cataracts, Graves' ophthalmopathy, haemangioma, herpes infections, neuropathies, retinal vasculitis, scleritis, for some gastrointestinal disorders, such as inflammatory bowel disease, nausea and oesophageal damage, for hypercalcaemia, infections, e.g. of the eye (as in infections mononucleosis), for Kawasaki disease, myasthenia gravis, various pain syndromes, such as postherpetic neuralgia, for polyneuropathies, pancreatitis, in respiratory disorders, such as asthma, for the management of rheumatoid disease and osteoarthritis, rhinitis, sarcoidosis, skin diseases, such as alopecia, eczema, erythema multiforme, lichen, pemphigus and pemphigoid, psoriasis, pyoderma gangrenosum, urticaria, in case of thyroid and vascular disorders.

The following examples and results of in-vitro and in-vivo studies shown in attached figures should illustrate the scope of the invention without setting or delineating its limits.

EXAMPLES 1–4

| Composition: | |
|---|---|
| 73.2 mg, 64.5 mg, 54.8 mg, 37.7 mg | Soy bean phosphatidylcholine (SPC) |
| 26.8 mg, 35.5 mg, 45.2 mg, 62.3 mg | Polysorbate (Tween 80) |
| 1 mg/g | Triamcinolone acetonide |
| 899 mg | Phosphate buffer (10 mM, pH 6.5) |

Preparation

Various SPC and triamcinolone acetonide amounts (as specified) are dissolved in 50 mL chloroform and 50 mL methanol. The solvent, which is kept warm (approx. 40 degrees Celsius), is evaporated under a stream of nitrogen and the residue is dried in vacuum at room temperature. Tween 80 in the specified quantity and phosphate buffer is added to the lipid film and the resulting crude suspension is sonicated to prepare smaller mixed lipid vesicles. The resulting suspension should be opalescent and slightly yellow, which requires up to a few minutes of sonication, and is stable for at least 1 day. The test sample is used within 24 h after the preparation.

Biological and/or Characterisation Experiments:

with this and all following suspensions were done as described further below.

EXAMPLES 4–5a AND 5b

| Composition: | |
|---|---|
| 37.74 mg | Soy bean phosphatidylcholine (SPC) |
| 62.26 mg | Tween 80 |
| 0.4 mg | Triamcinolone Acetonide |
| 0, 26.25 mg | Benzyl alcohol |
| 4.47 g | Phosphate buffer 50 mM pH 6.5 |
| 0.3 mg | Probucol |
| 0.3 mg | Desferal |

Preparation

SPC, probucol and triamcinolone acetonide are dissolved in a chloroform/methanol mixture. Dry lipid mixture is prepared as described for example 1. Desferal, Tween 80, and 894.23 mg buffer is added to the dry lipid. The resulting suspension is stirred over night. After adding, if so chosen, 26.25 mg benzyl alcohol in 3.58 g buffer to the suspension, the mixture is extruded through a 200 nm polycarbonate membrane and then through a 50 nm membrane using sufficient excess pressure to give an acceptable flow rate. The resulting particle diameter is below 150 nm.

EXAMPLE 6

| Composition: | |
|---|---|
| 37.74 mg | SPC |
| 62.26 mg | Tween 80 |
| 35 mg | Ethanol |
| 0.4 mg | Triamcinolone acetonide |

-continued

| Composition: | |
|---|---|
| 26.25 mg | Benzyl alcohol |
| 4.47 g | Phosphate buffer (50 mM pH 6.5) |
| 0.3 mg | Probucol |
| 0.3 mg | Desferal |

Preparation

SPC, probucol and triamcinolone Acetonide are dissolved in ethanol. Desferal, Tween 80, 5.25 mg benzyl alcohol and 894.23 mg buffer is added. The resulting suspension is stirred over night. The following day a solution of 21 mg benzyl alcohol in 3.58 g buffer is added to the suspension. The suspension is extruded, first, through a 200 nm pore polycarbonate membrane and then through a 50 nm membrane. This results in particle radius around 60 nm.

Analysis of formulation stability by means of HPLS suggests that the presence of probucol and desferal is advantageous to the chemical stability of suspension.

EXAMPLES 7–14

| Composition: | |
|---|---|
| 88.1 g, 87.4 g, 86.6 g, 85.75 g | Soy bean phosphatidylcholine (SPC) |
| 11.9 g, 12.6 g, 13.4 g, 14.25 g | Sodium cholate (NaChol) |
| 80 g | Ethanol |
| 0.5 g | Triamcinolone acetonide |
| ad 1000 g | Phosphate buffer (pH 7.1) |

Preparation

SPC and triamcinolone acetonide are dissolved in ethanol, to which NaChol is also added (which dissolves only partially). After the addition of buffer, the resulting turbid, whitish suspension is stirred over night. To bring the vesicles to final size, the suspension is either: extruded through a 200 nm membrane and then through a 100 nm membrane under pressure; 2) processed by a high pressure homogeniser (run in the low pressure range, e.g. at 200 psi) to yield an opalescent final suspension.

From the preparation made as described above, two alternative formulations were made by diluting the suspension with a buffer (containing 0.5 V-% benzyl alcohol) to a final total lipid concentration of 5 w-% and 2 w-%, respectively.

EXAMPLES 15–49

| Composition: | |
|---|---|
| 377.4 mg | Soy bean phosphatidylcholine (SPC) |
| 622.6 mg | Tween 80 |
| 50 mg | Benzyl alcohol |
| 9000 mg | Phosphate buffer 50 mM pH 6.5 |
| a) 12.5 mg, 25 mg, 50 mg, | Bethamethasone |
| b) 12.5 mg, 25 mg, 50 mg, | Bethamethasone dipropionate |
| c) 12.5 mg, 25 mg, 50 mg | Bethamethasone 17 valerate |
| d) 12.5 mg, 25 mg, 50 mg | Clobetasol-17-propionate |
| e) 12.5 mg, 25 mg, 50 mg | Dexamethasone or |
| f) 25 mg, 50 mg, 75 mg, | Hydrocortisone |

-continued

| Composition: | |
|---|---|
| g) 12.5 mg, 25 mg, 50 mg | Prednicarbate |
| h) 0.75 mg, 12.5 mg, 25 mg | Triamcinolone |

Preparation

SPC and the corticosteroid of choice is dissolved in ethanol. After the addition of buffer, which also contains Tween 80 and benzyl alcohol, the resulting highly turbid suspension is thoroughly mixed for at least 24 h, and more preferably for several days. The suspension is then extruded through a 200 nm membrane, if required several times. The resulting suspension of vesicles, which are still relatively large, tends to sediment with time, however, but can be re-homogenised easily by swirling or another gentle mixing method. To get vesicles with smaller final size, and thus a more stable suspension, a final extrusion through a 100 nm membrane is useful. (Vesicles with the highest given drug concentration may contain some drug in the suspension, perhaps in the form of vesicle coated drug crystals.)

EXAMPLE 50

| Composition: | |
|---|---|
| 347 mg | Soy bean phosphatidylcholine (SPC) |
| 623 mg | Tween 80 |
| 30 mg | Sodium dodecyl sulphate (SDS) |
| 50 mg | Benzyl alcohol |
| 9000 mg | Phosphate buffer 50 mM pH 6.5 |
| 25 mg | Clobetasol-17-propionate |

Preparation

Corticosteroid suspension was prepared as described in previous examples, except in that SDS was added dissolved in buffer to act as drug distribution promotor in the target organ.

Formulation containing SDS acts significantly more rapidly in human skin blanching assay than the SDS-free formulation.

Hereinfurther are described some preclinical experiences with the hydro-lotion-like formulations based on highly adaptable agent carriers, i.e. highly adaptable and flexible lipid vesicles (Transfersomes™; cf. above-cited references) of several corticosteroids in vitro and in vivo. These novel, carrier-based formulations are shown to give rise to the desired drug concentrations in the skin after a single application of the agent in Transfersomes. Depending on amount of carrier used, a localized (intracutaneous) or a local and systemic (whole body) delivery is possible.

The new corticosteroid delivery concept promises to lower the danger of adverse side effects of the topical therapy with such medication. This is possible due to dose-lowering and a different drug delivery mechanism: Corticosteroids in Transfersomes can not penetrate directly into the blood vessels, owing to the prohibitively large size of the carriers. Such drugs are thus confined to the intercellular space, where they can exert their desired biological function. (Only when they are applied in ample amounts such therapeutics are distributed throughout the body, first via the lymphatic and then through blood circulation.)

Data measured in animals and humans suggest that several widely used corticosteroids can be nearly prevented from reaching the blood if they are placed on the skin in a suspension of Transfersomes. One can argue that this phenomenon relies on the extremely high deformability of transfersome membranes, which permits the drug carriers to pass the skin permeability barrier. The good control over this penetration process and the exclusion of intravasation enables the restriction of the biological effects of transfersomal corticosteroids nearly exclusively to the treated skin. The different vaso-constriction induced by corticosteroids in creams/lotions or Transfersomes indirectly support this conclusion. The use of highly deformable carriers increases the potency of corticosteroids up to one order of magnitude in relation to previous, commercial formulations. This fact also improves the final drug safety. (The area-dose needed for the Transfersomes-mediated therapeutic success of dexamethasone or triamcinolone acetonide in the treated skin surface must reach 1.5 $m^2$ before the total applied drug amount matches that of native hydrocortisone in the blood.)

In vitro Penetration Studies

The differential penetration capability of various drug and drug-carrier formulations through an artificial transport barrier clearly demonstrates the relative advantage of ultradeformable Transfersomes in comparison with, for example, standard liposomes. While the latter are nearly completely incapable of crossing such an artificial 'skin barrier', Transfersomes pass through the fine openings in such a barrier essentially unhindered. The following table illustrates this behavior.

Table 1: Capability (relative to water) of the corticosteroid-loaded Transfersomes, liposomes and micelles to penetrate through the pores 3–4 times smaller than the penetrant size under the influence of hydrostatic pressure.[a]

[a] The artificial barrier consisted of a polycarbonate membrane perforated by the pores of 100 nm diameter. Liposomes and Transfersomes had comparable size. The quoted transport efficacy corresponds to the ratio of aggregate-to-water transport rate measured under identical conditions (by HPLC and gravimetry, respectively).

| Formulation | Low pressure (0.2 MPa) | High pressure (0.9 MPa) |
|---|---|---|
| Micelles | 1.1 ± 0.1 | 1.1 ± 0.1 |
| Liposomes | ≦0.0001 | ≦0.001 |
| Transfersomes | ≦0.001 | 1 ± 0.1 |
| Liposomes with hydrocortisone | ≦0.0001 | ≦0.001 |
| Transfersomes with hydrocortisone | ≦0.001 | 1 ± 0.1 |
| Transfersomes with dexamethasone | ≦0.001 | 1 ± 0.1 |
| Transfersomes with triamcinolone-acetonide | ≦0.001 | 1 ± 0.1 |

When applied onto the intact skin surface, phospholipid suspensions are not detrimental to the skin. On the contrary: certain phospholipid preparations have been reported to improve the hydration (and thus to a minor extent the optical appearance) of the aging skin. Phospholipid suspensions are also non-irritating to the skin, at least up to the degree of 30% degradation.

Corticosteroid preparations on the basis of transfersomes will normally be used in a quantity (around 100 mg per 2 days) that will contain lipid amounts comparable to those used parenterally (≦75 mg/injection) or orally (≦150 mg/day). The recommended daily dose of transfersomal corticosteroids for human use will be appreciably lower ($\leq 25$ mg), except in the case of hydrocortisone, where a somewhat higher dosage might be required for a whole body therapy.

Total phospholipid amount to be placed on the skin in the form of transfersomes-based corticosteroid formulations will always be less than 0.5 g/day. It is also less than 10% of the natural variability of phosphatidylcholine concentration in the plasma of an average, healthy person. In light of these data given below, one can conclude that the corticosteroidal dermatics based on transfersomes from the carrier point of view will be an extremely safe product.

From the agent point of view, a maximum corticosteroid amount (1 mg/day for dexamethasone or triamcinolone-acetonide and below 20 mg for hydrocortisone) comparable to that produced in the body (12 mg to 30 mg of hydrocortisone per day) will be applied topically. The area dose will normally be between 0.1 μg cm$^{-2}$ and 1 μg cm$^{-2}$, for the high and low potency drugs, respectively. Only a tiny fraction of the epicutaneously drug is likely to appear in the circulation, however, as can be seen from the following table.

The bidistilled water in injectable quality was purchased from the local pharmacy. The commercial drug formulations from the local pharmacy were used for comparison (hydrocortisone: Hydrocortisone-Wolff (Wolff, Bielefeld); dexamethasone: Anemul (Pharmasal, Gräfelfing); triamcinolon-acetonide: Volon A Lotio N (Squibb-Hayden, München) and Delphicort-cream (Lederle, Wolfratshausen)).

Drug in the Carrier (Transfersome) Suspensions. The formulations used in the biodistribution studies were labelled with the tritiurated corticosteroids purchased from Amersham or ICN. Preparation of the formulations for the use in animals was done by dissolving all lipoids in methanol/chloroform (1/1 v/v) in the appropriate amounts and preparing a dry mixed lipid film under vacuum ($\leq 10$ Pa; $\geq 12$ h). The use of potentially harmful organic solvents or drying was entirely avoided in the manufacturing of human medications.

Formulations contained between 0.01 w-% and 0.5 w-% specified corticosteroid per mL of carrier suspension. The latter consisted chiefly of phosphatidylcholine (SPC) in a

TABLE 2

The ratio of corticosteroid concentration in the blood and in the 'inner skin' of mice (measured) and humans (calculated).

| Dose (μg/cm$^{-2}$) | Hydro-cortisone (mouse) | Hydro-cortisone (human) | Dexa-methasone (mouse) | Dexa-methasone (human) | Triamcinol-one-acetonide (mouse) | Triamcinol-one-acetonide (human) |
|---|---|---|---|---|---|---|
| 0.5 | 0 | 0 | 0 | 0 | | |
| 1.3 | | | | | 0.02 | 0.00007 |
| 4.9 | 0.012 | 0.000004 | 0.1 | 0.00003 | | |
| 13.2 | | | | | 0.04 | 0.00011 |
| 20.6 | | | | | 0.03 | 0.0001 |
| 49.5 | 0.015 | 0.000005 | 0.25 | 0.00009 | | |

It can, therefore, be anticipated that corticosteroids based on transfersomes will cause less side effects, if any, than the currently available commercial formulations of such drugs. This, on the one hand, is due to the more favorable biodistribution of the drugs from the transfersomes, which is concentrated to the tissue to be treated. On the other hand, drugs from the carriers are likely to be taken in relatively higher proportions by the strongly proliferating cells, which are one of the chief natural targets for the corticosteroid therapy. (It is even possible that very low doses of transfersomal corticosteroids will completely eliminate the problem of skin atrophy after the repeated use of such therapeutics.)

Even more relevant, for the assessment of practical values of transfersomal corticosteroids, are the results obtained in validated animal trials, which are described in the following section.

Preclinical Studies

All substances used in this study were of pharmaceutic quality. Soybean phosphatidylcholine (SPC) was purchased from Lipoid KG (Ludwigshafen, Germany) or Nattermann Phospholipids—Rhone-Poulenc Rorer (Köln, Germany) and was more than 95% pure. The remaining components, which are described in detail in the above cited European patent, were from Henkel (Düsseldorf, Germany) or CPC (Hamburg, Germany). The active ingredients (dexamethasone, hydrocortisone, triamcinolone-acetonide) were purchased from Synopharm (Hamburg, Germany). The microbicides, chellators and antioxidants were from Ciba-Geigy (Basel, Switzerland) or Synopharm.

final concentration between 0.5 w-% and 5 w-%. This lipid was was taken up in a buffer and homogenized (for animal experiments: by sonication with a titanium micro-tip, Heat Systems W 380, USA, 30 min, 4° C.; for human therapeutics by other mechanical means). At least one of the carrier components was characterized by its membrane solubilizing capacity, as is required by the basic rationale of Transfersome design and above-cited patent applications of the applicant. Such a embrane-affecting substance was always incorporated into the carriers in the sub-lytic concentration. This ensured the high carrier deformability without compromising the integrity of transfersome vesicles, since both is necessary for the high efficacy of drug carrier transport across the stratum corneum. The final vesicle size was determined with the photon correlation spectroscopy (90°, ALV-5000 ALV-Laser Vertriebsgesellschaft, Langen, Germany) and was typically between 100 nm and 200 nm. For experimental use, lipid suspension was diluted when appropriate. More detailed description and characterization data will be given separately.

In vivo Experiments mainly involved 8–12 weeks old NMRI mice which were kept under standard laboratory conditions (3–5 per suspending cage; standard chew and water ad libitum; 12 h light/dark regime). Stressful or painful manipulations were always carried out under general injection anesthesia.

Biodistribution. The hair at the chosen skin site was trimmed with a pair of scissors to the length of $\leq 2$ mm one day before experimentation. The precise application site on the upper back was marked and the appropriate amount (0.5

µL to 25 µL) and drug formulation was applied with a micro-pipette on the skin. After uniform distribution with the side of the same pipette tip, the application was left to dry.

Blood samples (20 µL) were taken from the tail end with a glass capillary. After 8 hours the animals were killed by heart puncture and the treated skin area was undermined and carefully excised. The outermost layers of the stratum corneum were collected by five tape-strippings. Subsequently, the residual skin tissue and other organ samples were prepared, destained and used for radioactivity counting. For the experiments with porcine skin, 20×30 cm² of full thickness organ was excised and fixed on a wet tissue. Several test areas of 1 cm² were then marked and treated further as in vivo.

Biological Action in mice was most often tested by measuring the suppression of a chemically induced edema by the topically administered corticosteroids. For this purpose, the test animals were first anesthetized with an intraperitoneal injection of 10 µL $g^{-1}$ body weight of a mixture containing 6 mL 0.9% NaCl, 1 mL Ketavet 100 (Parke-Davis, Berlin, FRG), and 0.25 mL Rompun (Bayer, Leverkusen, Germany). The appropriate amount of drug formulation was smeared over the inner side of one ear and left to dry out. When so treated, the ear was wiped free of the superficial formulation with a cotton swab. At a given time the test mouse was anesthetized and arachidonic acid in ethanol (½ V/V, 10 \muL) was applied to the same ear area. Change in the mouse ear edema (relatively to that of the untreated but challenged ear) was determined, either by measuring the ear thickness with a micro-caliper (our method) or by weighing the ear volume of the killed mouse (original procedure). Both these assays deliver similar results. All values are the means of at least 3 independently measured values and bars give standard deviation of their mean.

Human Studies

According to the scientific literature, it is customary to test the biological potency of different corticosteroid preparations in humans by a so-called 'skin blanching' assay. Such a test is not as adequate for the investigation of carrier-based corticosteroids, as it is for the testing of the corresponding drug solutions for the reasons given below. This notwithstanding, the topical vaso-constriction test was used to compare the kinetics of corticosteroid action on the rodent and human skin.

In a pilot trial with three human volunteers, the test formulations were applied to one arm at different doses in parallel rows. By using a high precision micropipette, individual areas of 1 cm² were covered. The vaso-constriction over each such skin domain was then determined by visual inspection (at least once by an independent observer who was unaware of the drug application pattern) and the skin blanching score was identified with the number of well defined square corners or edges.

Figure 4:
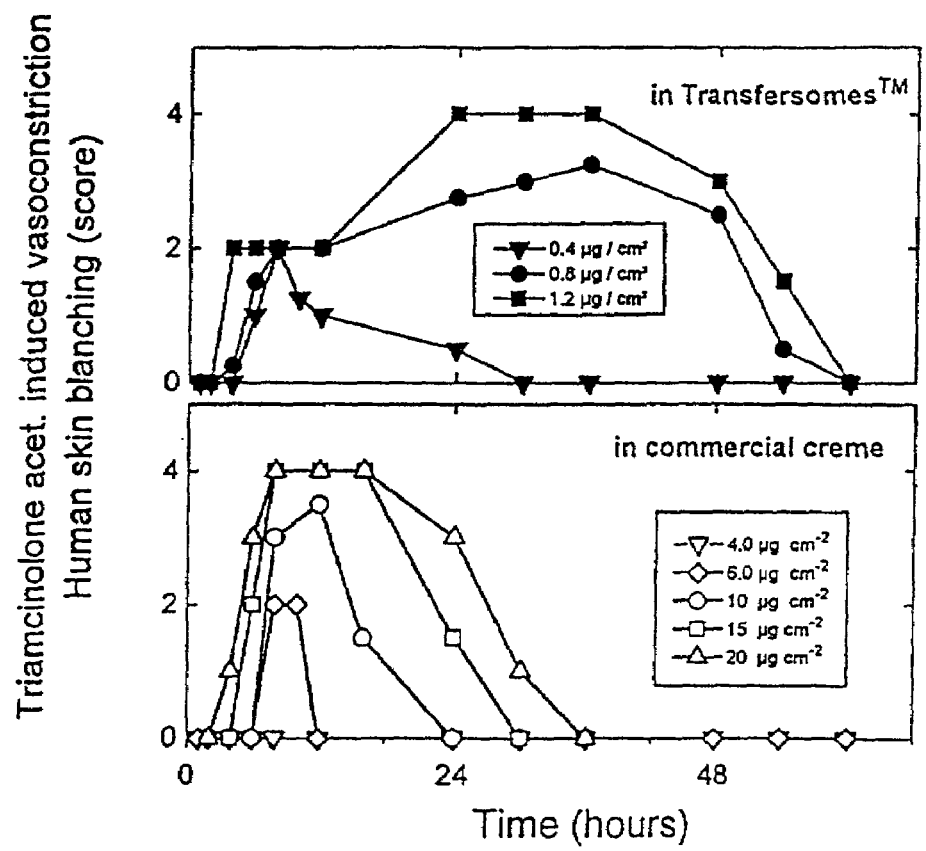
FIG. 4 presents the results of dose and time dependence measurements for triameinolone-acetonide applied in a commercial creme (open symbols) or in Transfersomes (closed symbols) on one forearm of a healthy human volunteer. The read-out was the extent of skin blanching caused by the drug, a the tested doses as given in insets.

Human skin was shown to respond similarly to the topical administration of corticosteroids in Transfersomes when compared to murine skin: after approximately 7 h the vaso-constriction (skin blanching) effect reaches 50% of its maximum value and saturates at $t \geq 8$ h. A high biological activity is observed for at least 32 h, with final decay to 50% level observed between 36 h and 48 h, provided the administered drug dose is around 1 µg $cm^{-2}$ (FIG. 4).

Similar evolution of skin blanching is observed after the topical administration of triamcinolone-acetonide in a commercial cream, but not before the drug dose has exceeded 10 µg $cm^{-2}$. Skin palor in the early phase ($8 \leq t/h \leq 16$) after cream application is deeper (whiter) and appears faster than in the case of the cortico-Transfersomes-mediated vaso-constriction. In our opinion, this is due to the restricted ability of transfersome-associated drugs to get into the blood capillaries. This phenomenon is not encountered with the drugs in commercial formulations, which allow diffusiong through and beyond the skin in monomeric (or at least dissociated) form. This explains the faster onset of (the desired) edema-suppression action and the retardation of (the rather undesired) vaso-constriction, which is an indication of drug spill-over into the blood circulation. (The relatively sluggish appearance of Transfersomes-mediate edema-suppression is also due to the poor responsiveness of one test person, who reacted to the drug in Transfersomes slowly and did not react to the low dose of commercial creme at all, the latter lack of effect not being seen in the time-course of average drug action.)

Results from the representative experiments are shown in the attached figures.

Upper panel of FIG. 1 illustrates the biological edema-suppression activity of hydrocortisone in commercial cream (open symbols) and in the highly adaptable lipid vesicles, Transfersomes, (closed symbols). Data give mean values measured from 3–4 animals and error bars represent the corresponding standard deviations.

Lower panel of FIG. 1 shows dose versus action, as assessed in the local edema-suppression tests, of hydrocortisone in a commercial cream (open symbols) and transfersomal suspension (closed symbols) after 16 h of action. (The maximum in dose vs. action curve is due to the dose dependence of action kinetics (see also FIG. 2).)

From FIG. 1 can be seen that the biological effect of hydrocortisone in Transfersomes™-based formulation significantly exceeds that of the more conventional cream-like formulation containing similar drug—the lower is the administered drug-dose per area the higher is the resulting therapeutic advantage. These data suggest that it should be possible to make, and sell with an excellent commercial perspective, the (hydro)lotion-like hydrocortisone formulation containing just 0.1% of the drug. This unprecedented low agent content may reduce the danger of side effects.

Figure 2:
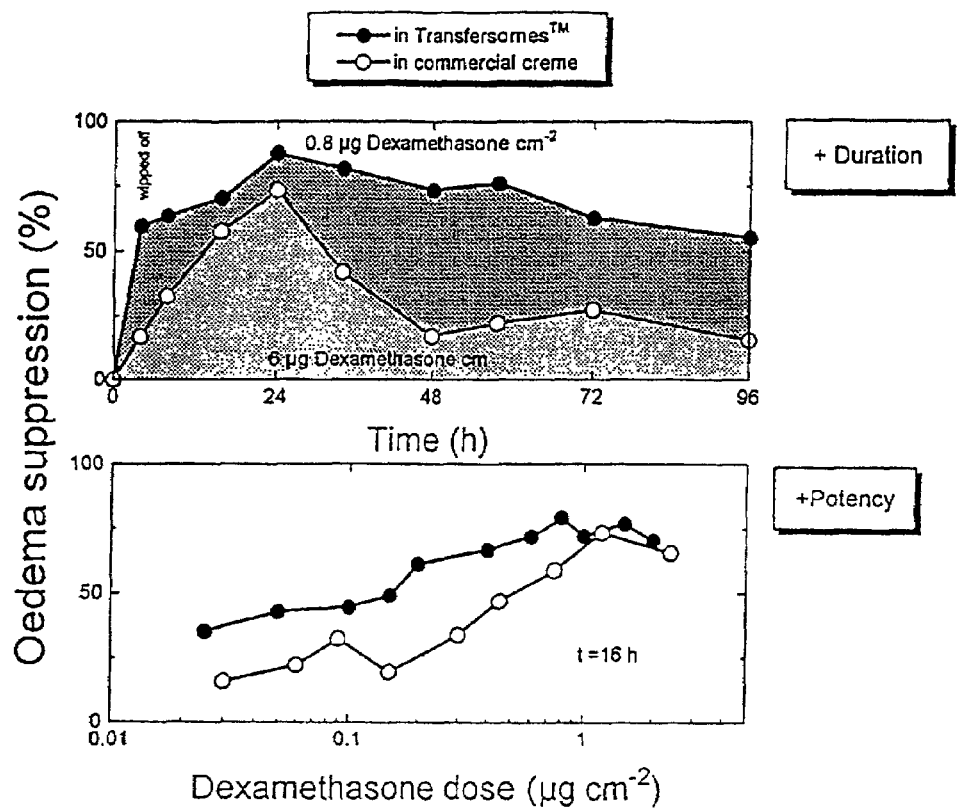
FIG. 2 illustrates the suppression of the arachidonic acid-induced oedema by dexamethasone in a commercial creme (open symbols) or in Transfersomes (closed symbols) as a function of the time after drug administration (upper panel) or of the epicutaneously applied drug dose (lower panel).

Upper panel of FIG. 2 illustrates suppression of the arachidonic acid-induced edema by dexamethasone in the commercial cream (open symbols) or Transfersomes (closed symbols) as the function of time after drug administration on the intact murine skin. In both cases the excess drug was wiped-away from the application site 8 h after administration.

Lower panel shows effect of changing the dose per area on the dexamethasone-mediated suppression of skin edema in the murine ear model. (Different symbols give results from the different experimental series; for further details see FIG. 1.)

As a result from FIG. 2 it is obvious that owing to its higher intrinsic potency, dexamethasone exerts a much stronger biological effect than hydrocortisone when tested locally on the challenged skin. The incorporation of dexamethasone into the ultradeformable agent carriers, Transfersomes further improves this therapeutic advantage. The benefit of using Transfersomes is most dramatic when the excess drug is eliminated from the treated skin site (as in real life). It is expected that drug formulations with merely 0.02% dexamethasone ('strong') or with just around 0.005% dexamethasone ('gentle') in Transfersomes will be needed for an adequate skin treatment.

Figure 3:
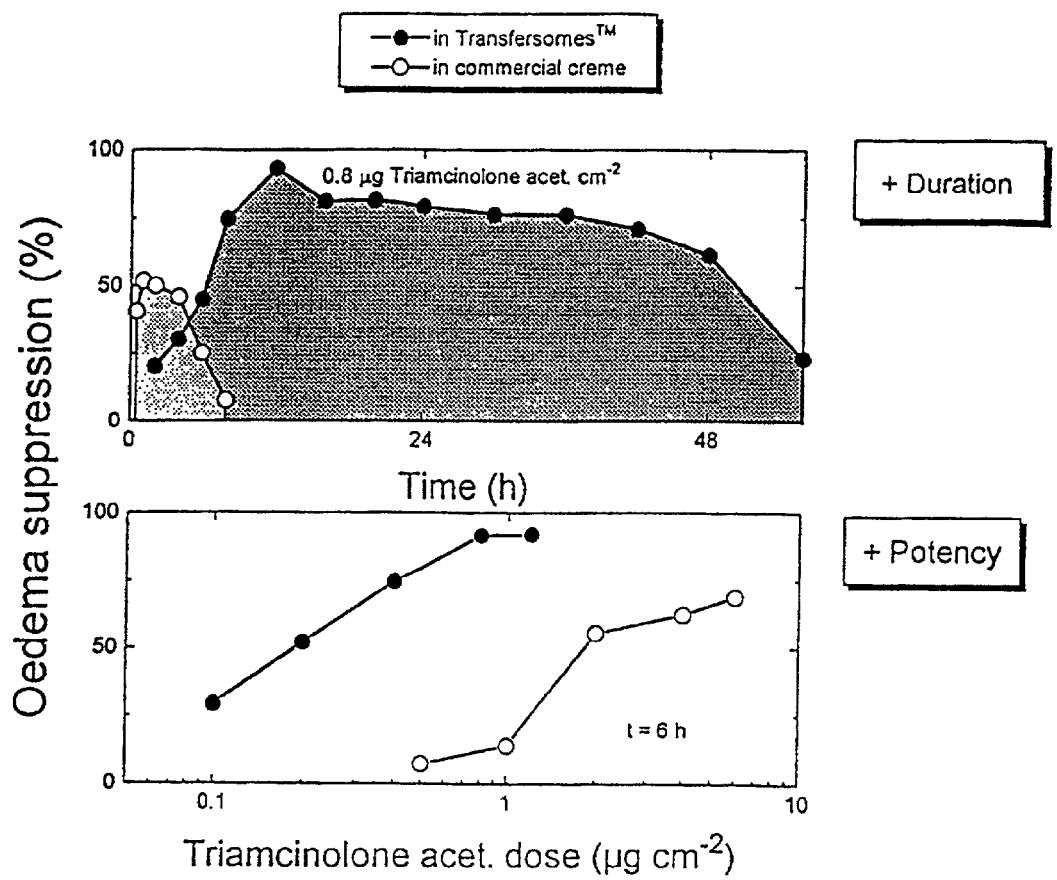
FIG. 3 provides information related to that given in FIGS. 1 and 2, but pertaining to a different glucocorticosteroide, triameinolone acetonide.

Upper panel of FIG. 3 illustrates the biological anti-edema activity of triamcinolone-acetonide in commercial lotion (open symbols) or in Transfersomes (closed symbols) in the murine ear model whereas lower panel shows dose vs. action curve for triamcinolone-acetonide in Transfersomes (full symbols, two different preparations and test series), commercial cream (open boxes) or commercial lotion (open circles) applied on the intact murine skin.

The biological potency of triamcinolone-acetonide in commercial products is thus 10-times lower than that of the drug in a suspension of Transfersomes. The latter also prolong the duration of therapeutic effect by the same order of magnitude. In comparison with transfersomal dexamethasone, triamcinolone-acetonide in the ultradeformable agent carriers exerts a somewhat stronger but moderately less persistent biological function. The anticipated drug concentration for the commercial formulation on the basis of Transfersomes is between 0.005% and 0.02%.

FIG. 4 shows vaso-constriction (blanching-assay) in the intact human skin as a function of time, following an epicutaneous administration of triamcinolone-acetonide in Transfersomes (upper panel) or in commercial cream (lower panel).

It thus can be seen that the 'therapeutic effect' on the human skin of the high potency corticosteroid applied in Transfersomes is dramatically better than that of the conventional triamcinolone-acetonide cream. A single topical drug administration with Transfersomes ensures good biological function for more than a day, with a dose of 1 µg cm$^{-2}$. While the commercial cream causes a rather short-term 'deep blanching', the Transfersomes-based formulations mediates a more gradual and long-lasting superficial vaso-constriction. This is indicative of reduced drug spill-over into the circulation from the carrier-based formulation (see also the figures on the following two pages).

Figure 5:
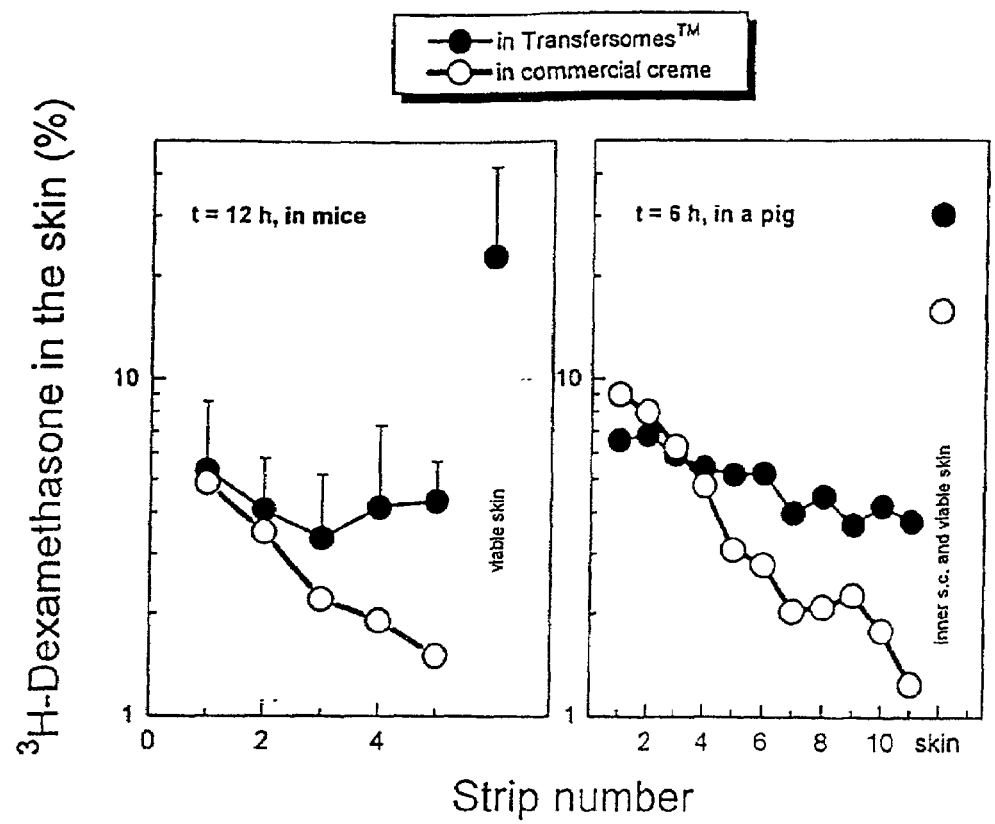
FIG. 5 shows dexamethasone penetration profile in murine skin in vivo (left panel) or in a pig skin ex vivo (right panel). Open symbols were measured with a commercial creme and closed symbols with the suspension of dexamethasone-loaded Transfersomes.

In FIG. 5 differerent drug penetration profiles in the mammalian skin are shown. The data were measured in vivo in mice (left panel) and ex vivo in porcine skin (right panel). Open symbols represent measurements with a commercial cream and closed symbols with the suspension of dexamethasone-loaded Transfersomes.

The use of Transfersomes for carrying corticosteroids in the skin flattens the drug penetration profile in the skin. The relative drug concentration increases in the deeper skin region, when compared to the results achieved with the commercial formulation of similar drug.

Figure 6:
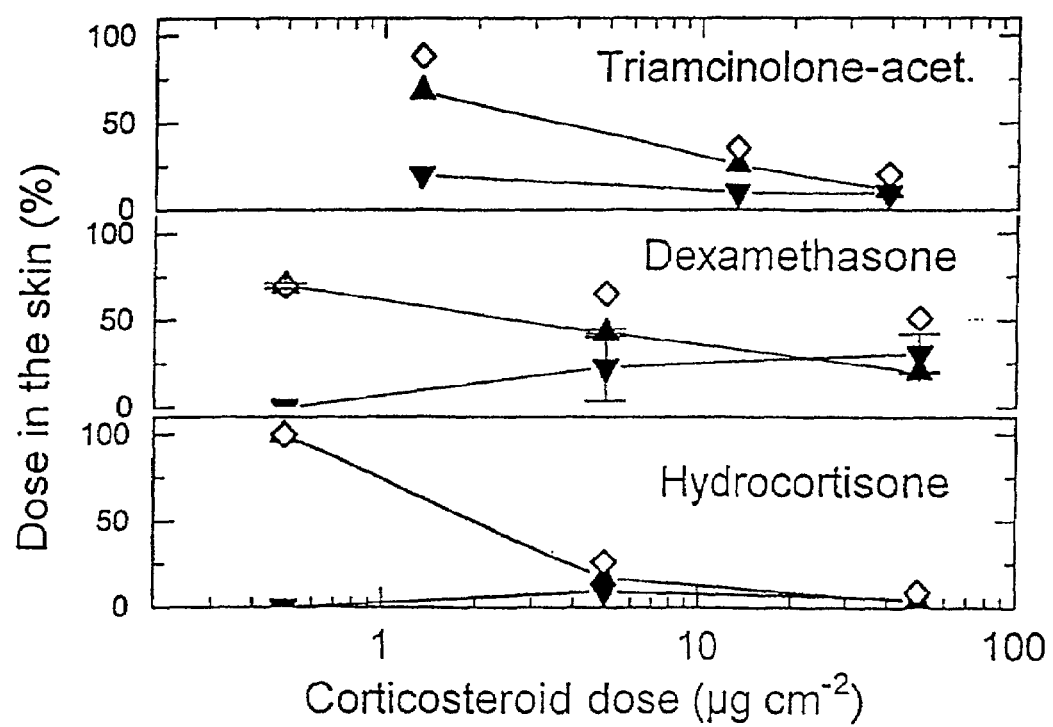
FIG. 6 demonstrates the level of corticosteroid accumulation (retention) in the skin after different drugs' application on the organ surface by means of Transfersomes (closed down-arrow: the stratum corneum; closed up-arrow: the skin stripped free of the stratum corneum; open diamond: total drug amount in the entire skin (=the sum of the former two).

FIG. 6 illustrates corticosteroid accumulation (retention) in the skin after administration by means of Transfersomes on the intact surface. (∇ and Δ correspond to the inner and outer skin regions and ◇ gives their sum.)

As a result transfersomes bring a relatively high proportion of the epicutaneously administered drug into the viable skin.

Figure 7:
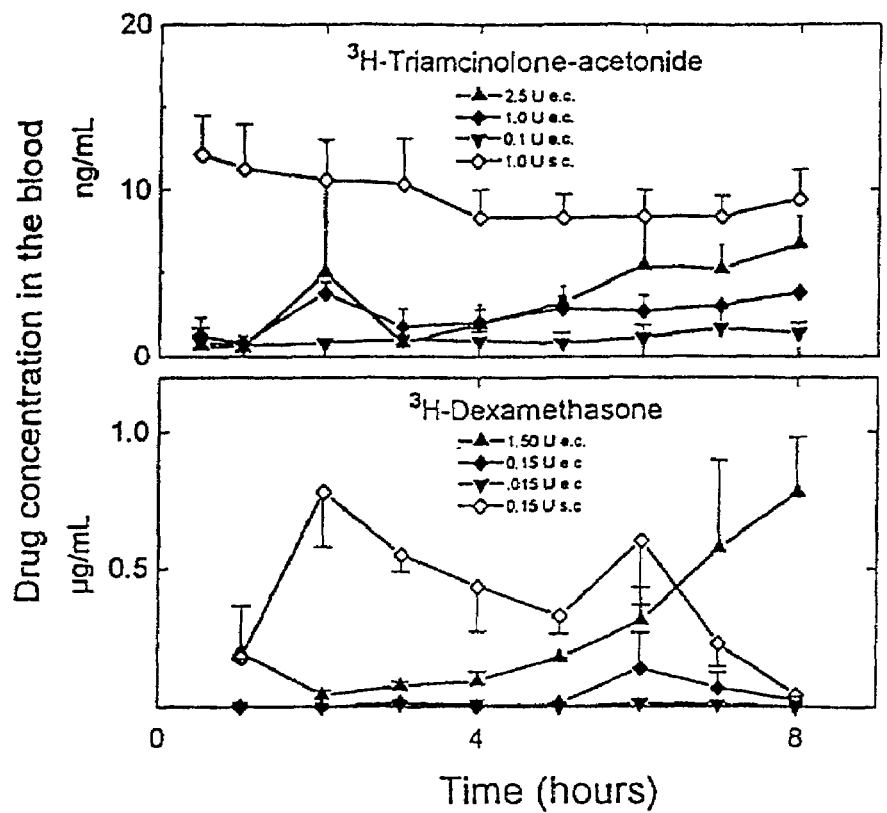
FIG. 7 illustrates (pharmaco)kinetics of transcutaneous transport of various corticosteroids, as assessed by measuring the drug derived radioactivity in the serum, following the topical drug administration with ultradeformable vesicles on (closed symbols) or under (open symbols) intact murine skin. Data points give the mean values for 3–4 animals and vertical bars give standard error of the mean. The applied drug dose in relative units is given in insets.

FIG. 7 illustrates using of Transfersomes for the transcutaneous corticosteroid delivery into the systemic circulation.

Choosing suitably optimized agent carriers (good Transfersomes) as well as proper dose per area allows for systemic delivery. Lowering the dose per area increases the relative drug concentration at the site of epicutaneous carrier administration.

Figure 8:
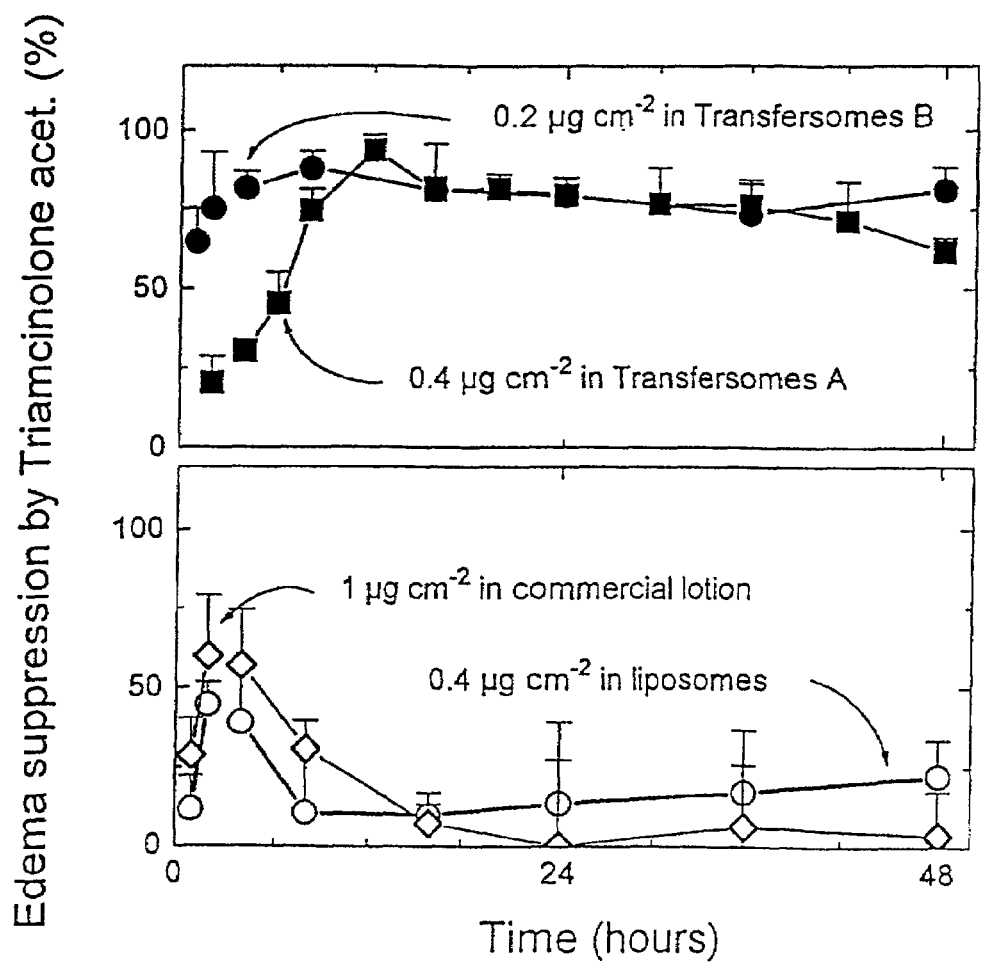
FIG. 8 provides some representative data on biological, anti-oedema activity of triamcinolone-acetonide applied on the skin in a commercial lotion or in conventional lipid vesicles, liposomes (lower panel) or else in highly deformable mixed lipid vesicles, Transfersomes (upper panel). All results were determined in the arachidonic acid induced murine ear oedema model. The topically applied doses are given in the panels. Formulation B was based on oleic acid rather than on phospholipids, as the main carrier ingredient.

In FIG. 8 relative efficiency of various triamcinolone acetonide formulations as tested by the murine ear edema assay is shown. Comparison of the biological activity of two different kinds of Transfersomes loaded with this drug (upper panel), a commercial cream (lower panel) and of conventional liposomes (lower panel). The latter two data sets are not statistically significant even at the level of 0.1.

In order to maximize the efficacy of intracutaneous drug delivery and to achieve good biological effects it is necessary to employ the specially optimized, proprietary agent carriers, Transfersomes. The replacement of such highly deformable Transfersomes by simple, conventional liposomes produces results that are not better than those obtained by the commercial creams (or lotions).

Appendix A

PCT International Search Report;
PCT Written Opinion;
PCT Response to Written Opinion (with Article 19 Amendments);
PCT International Preliminary Examination Report;
Abstract on a separate sheet;
Information Disclosure Statement;
Form PTO 1449;
Copies of References Cited; and
Postcard

The invention claimed is:

1. A formulation comprising penetrants being capable of penetrating the pores of a barrier, the average diameter of said pores being smaller than the average diameter of said penetrants, wherein said penetrants can transport agents or enable agent penetration through said pores after said penetrants have entered said pores, wherein the formulation further comprises
   1) at least one antioxidant in an amount that reduces the increase of oxidation index to less than 100% per 6 months, wherein the antioxidant is selected from the group consisting of between 0.0025 and 0.2 w-% of butylated hydroxyanisol, between 0.0025 and 0.2 w-% of butylated hydroxytoluene, between 0.001 and 2 w-% of tertiary butylhydroquinone, between 0.001 and 2 w-% of propyl gallate, between 0.005 and 5 w-% of tocopherols, between 0.001 and 5 w-% of ascorbic acid esters, between 0.001 and 5 w-% of ascorbic acid, between 0.001 and 5 w-% of sodium bisulphite, between 0.001 and 5 w-% of sodium metabisulphite, between 0.0001 and 2 w-% of thiourea, between 0.01 and 5 w-% of cysteine, between 0.01 and 5 w-% of monothioglycerol, between 0.0005–2 w-% of nordihydroguaiaretic acid, between 0.005 and 5 w-% of glutathione, between 0.001 and 5 w-% of EDTA, and between 0.001 and 5 w-% of citric acid, based on the total weight of the formulation; and
   2) at least one microbiocide in an amount that reduces the bacterial count of 1 million germs added per gram of total mass of the formulation to less than 100 in the case of aerobic bacteria, to less than 10 in the case of entero-bacteria, and to less than 1 in the case of *Pseudomonas aeruginosa* or *Staphilococcus aureus*, after a period of 4 days, wherein the microbicide is selected from the group consisting of up to 10 w-% of ethyl alcohol, up to 10 w-% of propyl alcohol, up to 10 w-% of butyl alcohol, up to 10 w-% of benzyl alcohol, between 0.3–0.6 w-% of chlorobutanol, between 0.05–0.2 w-% of parabens, between 0.05–0.2 w-% of methyl paraben, between 0.002–0.02 w-% of propyl paraben, between 0.05–0.2 w-% of sorbic acid, between 0.1–0.5 w-% of benzoic acid, between 0.1–0.3 w-% of phenols, between 0.1–0.3 w-% of triclosan, and between 0.01–0.05 w-% of chlorhexidine, based on the total weight of the formulation;

wherein the agent is selected from corticosteroids and the relative content of corticosteroids is above 0.1 weight-%, relative to total dry mass of the formulation.

2. The formulation according to claim 1, wherein said at least one antioxidant is added in an amount that reduces the increase of oxidation index to less than 100% per 12 months.

3. The formulation according to claim 1, further comprising at least one consistency builder, in an amount that increases the formulation viscosity above that of the non-thickened corresponding formulation to maximally 5 Ns/m$^2$ so that spreading over, and retention at, the application area is enabled.

4. The formulation according to claim 3, wherein said at least one consistency builder is added in an amount that increases the formulation viscosity to up to 1 Ns/m$^2$.

5. The formulation according to claim 3, wherein the consistency builder is selected from the group consisting of:
pharmaceutically acceptable hydrophilic polymers; completely synthetic hydrophilic polymers; natural gums; and mixtures and further derivatives or co-polymers thereof.

6. The formulation according to claim 5, wherein the polymer weight fractions are in the range between 0.05% and 10%.

7. The formulation according to claim 5, wherein the pharmaceutically acceptable hydrophilic polymers are selected from partially etherified cellulose derivatives, comprising carboxymethyl-, hydroxyethyl-, hydroxypropyl-, hydroxypropylmethyl-, or methyl-cellulose.

8. The formulation according to claim 5, wherein the completely synthetic hydrophilic polymers are selected from polyacrylates, polymethacrylates, poly(hydroxyethyl)-, poly(hydroxypropyl)-, poly(hydroxypropylmethyl)methacrylate, polyacrylonitrile, methallyl-sulphonate, polyethylenes, polyoxiethylenes, polyethylene glycols, polyethylene glycol-lactide, polyethylene glycol-diacrylate, polyvinylpyrrolidone, polyvinyl alcohols, poly(propylmethacrylamide), poly(propylene fumarate-co-ethylene glycol), poloxamers, polyaspartamide, hydrazine cross-linked hyaluronic acid and silicone.

9. The formulation according to claim 5, wherein the natural gums are selected from alginates, carrageenan, guar-gum, gelatine, tragacanth, amidated pectin, xanthan, chitosan collagen and agarose.

10. The formulation according to claim 1, wherein the corticosteroid is selected from the group consisting of: alclonetasone dipropionate, amcinonide, beclomethasone dipropionate, betamethasone, betamethasone 17-valerate, betamethasone 17,21-divalerate, betamethasone 21-acetate, betamethasone 21-buytrate, betamethasone 21-propionate, betamethasone 21-valerate, betamethasone benzoate, betamethasone dipropionate, betamethasone valerate, budesonide, clobetasol propionate, clobetasone butyrate, cortexolone, corticosterone, cortisone, cortisone 17-acetate, 21-deoxybetamethasone, 21-deoxybetamethasone 17-propionate, deoxycorticosterone, desonide, desoxymethasone, dexamethasone, diflorasone diacetate, diflucortolone valerate, fluclorolone acetonide, flumethasone pivalate, fluoconolone acetonide, fluocinonide, fluocortin butyl, fluocortolone, 9-alpha-fluorocortisone, 9-alpha-fluorohydrocortisone, 9-alpha-fluoroprednisolone, fluprednidene acetate, flurandrenolone, halcinonide, hydrocortisone, hydrocortisone 17-acetate, hydrocortisone 17-butyrate, hydrocortisone 17-propionate, hydro cortisone 17-valerate, hydrocortisone 21-acetate, hydrocortisone 21-butyrate, hydrocortisone 21-propionate, hydrocortisone 21-valerate, 17-alpha-hydroxyprogesterone, methylprednisolone acetate, mometasone furoate, prednisolone, prednisone, prednisone 17-acetate, prednisone 17-valerate, progesterone, triamcinolone, and trimcinolone acetonide.

11. The formulation according to claim 1, wherein the penetrants are suspended or dispersed in a polar liquid in the form of fluid droplets surrounded by a membrane-like coating of one or several layers, said coating comprising at least two kinds or forms of amphiphilic substances with a tendency to aggregate,
wherein said at least two substances differ by at least a factor of 10 in solubility in said liquid or wherein said substances when in the form of homo-aggregates, for the more soluble substance, or of hetero-aggregates, for any combination of both said substances, have preferred average diameter smaller than the diameter of the homo-aggregates containing merely the less soluble substance; or
wherein the presence of the more soluble substance lowers the average elastic energy of the membrane-like coating in the vicinity of thermal energy.

12. The formulation according to claim 11, wherein the average penetrant diameter is between 30 nm and 500 nm.

13. The formulation according to claim 11, wherein the average diameter of the penetrant is 2 to 25 times bigger than the average diameter of the pores in the barrier.

14. The formulation according to claim 11, wherein the dry weight of all carrier droplets in a formulation for the use on human or animal skin is 0.01 weight-% (w-%) to 40 w-% of total formulation mass.

15. The formulation according to claim 11, wherein the dry weight of all carrier droplets in a formulation for the use on human or animal mucosa is 0.0001 w-% to 30 w-% of total formulation mass.

16. The formulation according to claim 1, wherein the content of corticosteroids is between 0.1 w-% and 20 w-%.

17. The formulation according to claim 16, wherein the relative content of corticosteroids is the case of clobetasol or one of its derivatives is below 15 w-%, relative to total dry mass of the drug-loaded carriers.

18. The formulation according to claim 16, wherein the content of said corticosteroid is below the saturation maximum, defined as the content of corticosteroid at which the corticosteroid begins to crystallize in or outside the carrier.

19. The formulation according to claim 1, wherein in order to speed up drug action a permeation enhancer is added.

20. The formulation according to claim 1, wherein said corticosteroid is added in an amount which enables the formulation to be applied corresponding to an area dose, as expressed by the total dry mass of penetrant applied per unit area, of between 0.1 mg cm$^{-2}$ and 15 mg cm$^{-2}$, if said corticosteroid is desired to exert a therapeutic effect in the deep subcutaneous tissue or the remote tissues, including the whole body.

21. The formulation according to claim 1, wherein said corticosteroid is added in an amount which enables the formulation to be applied with an area dose, as expressed by the total dry mass of penetrant applied per unit area, of between 1 µg cm$^{-2}$ and 250 µg cm$^{-2}$, if said corticosteroid is desired to exert a mainly local rather than systemic therapeutic effect.

22. The formulation according to claim 1, wherein consistency and, if necessary other characteristics of the formulation are appropriately selected to enable spraying, smearing, rolling or sponging of the formulation on the application area in particular by using a sprayer, spender, roller or sponge.

23. The formulation according to claim 1, wherein the concentration based on the total weight of the formulation of TBHQ and PG is between 0.005 and 0.2 w-%, of tocopherols is between 0.01 and 0.5 w-%, of ascorbic acid esters is between 0.005 and 0.5 w-%, of ascorbic acid is between 0.005 and 0.5 w-%, of sodium bisulphite or sodium metabisulphite is between 0.005 and 0.5 w-%, of thiourea is between 0.0005 and 0.2 w-%, of cysteine is between 0.05 and 2 w-%, of monothioglycerol is between 0.05 and 2 w-%, of NDGA is between 0.00 1 and 0.2 w-%, of glutathione is between 0.01 and 0.5 w-%, of EDTA is between 0.005 and 0.5 w-%, of citric acid is between 0.005 and 3 w-%.

24. The formulation according to claim 1, wherein the concentration based on the total weight of the formulation of BHA or BHT is between 0.005 and 0.02 w-%, of TBHQ and PG is between 0.01 and 0.02 w-%, of tocopherols is between 0.05 and 0.075 w-%, of ascorbic acid esters is between 0.01 and 0.15 w-%, of ascorbic acid is between 0.01 and 0.1 w-%, of sodium bisulphite or sodium metabisulphite is between 0.01 and 0.15 w-%, of thiourea is between 0.001–0.01 w-%, of cysteine is between 0.1 and 1.0 w-%, of monothioglycerol is between 0.1 and 1.0 w-%, of NDGA is between 0.005 and 0.02 w-%, of glutathione is between 0.05 and 0.2 w-%, of EDTA is between 0.01 and 0.2 w-%, of citric acid is between 0.01 and 0.2 w-%.

25. The formulation according to claim 1, wherein the concentration based on the total weight of the formulation of thiourea is 0.005 w-%, of cysteine is 0.5 w-%, of monothioglycerol is 0.5 w-%, of NDGA is 0.01 w-%, of glutathione is 0.1 w-%, of EDTA is between 0.05 and 0.975 w-%, of citric acid is between 0.3 and 2 wt-%.

26. The formulation according to claim 1, wherein the bulk concentration based on the total weight of the formulation of ethyl, propyl, butyl or benzyl alcohol is up to 5 w-%.

27. The formulation according to claim 1, wherein the bulk concentration based on the total weight of the formulation of ethyl, propyl, butyl or benzyl alcohol is in the range between 0.5–3 w.-%.

28. The formulation according to claim 1, wherein the at least one microbiocide is added in an amount that reduces the bacterial count of 1 million germs added per gram of total mass of the formulation to less than 100 in the case of aerobic bacteria, to less than 10 in the case of enterobacteria, and to less than 1 in the case of *Pseudomonas aeruginosa* or *Staphilococcus aureus*, after a period of 3 days.

29. The formulation according to claim 1, wherein the tocopherols are selected from tocopheryl-acrylate, -laurate, myristate, -palmitate, -oleate, -linoleate, or any other suitable tolopheryl-lipoate and tocopheryl-POE-succinate.

30. The formulation according to claim 1, wherein the ascorbic acids are selected from 6-o-lauroyl, myristoyl, palmitoyl-, oleoyl, or linoleoyl-L-ascorbic acid.

31. The formulation according to claim 1, wherein the phenols are selected from cresol, 4-chloro-m-cresol, p-chloro-m-xylenol, dichlorophene, hexachlrophene and povidon-iodine.

32. The formulation of claim 1, wherein the corticosteroids are selected from glucocorticoids or mineralocorticosteroids.

33. The formulation according to claim 1, wherein the corticosteroid is propionate.

* * * * *